US010179015B2

(12) United States Patent
Lavigne et al.

(10) Patent No.: US 10,179,015 B2
(45) Date of Patent: Jan. 15, 2019

(54) BONE IMPLANTS

(71) Applicant: LDR MEDICAL, Rosieres Pres Troyes (FR)

(72) Inventors: Christophe Lavigne, Austin, TX (US); Patrick Richard, Rancenay (FR); Alexis Mercier, Verrieres (FR); Samuel Lequette, Pessac (FR)

(73) Assignee: LDR Medical, Rosieres Pres Troyes (FR)

( * ) Notice: Subject to any disclaimer, the term of this patent is extended or adjusted under 35 U.S.C. 154(b) by 519 days.

(21) Appl. No.: 14/815,900

(22) Filed: Jul. 31, 2015

(65) Prior Publication Data

US 2016/0100870 A1    Apr. 14, 2016

(30) Foreign Application Priority Data

Aug. 1, 2014    (FR) ...................................... 14 57539

(51) Int. Cl.
*A61B 17/04*    (2006.01)
*A61B 17/86*    (2006.01)
(Continued)

(52) U.S. Cl.
CPC ........ *A61B 17/864* (2013.01); *A61B 17/7064* (2013.01); *A61B 17/7098* (2013.01);
(Continued)

(58) Field of Classification Search
None
See application file for complete search history.

(56) References Cited

U.S. PATENT DOCUMENTS 5,840,078 A    11/1998  Yerys
6,824,564 B2 *  11/2004  Crozet ................... A61B 17/86
                                                    623/17.11
(Continued)

FOREIGN PATENT DOCUMENTS

CA    2955131 A1    2/2016
EP    2589351 A1    5/2013
(Continued)

OTHER PUBLICATIONS

"U.S. Appl. No. 15/501,166, Preliminary Amendment filed Feb. 1, 2017", 13 pgs.
(Continued)

*Primary Examiner* — Sameh Boles
(74) *Attorney, Agent, or Firm* — Schwegman Lundberg & Woessner, P.A.

(57) ABSTRACT

The present disclosure provides various embodiments that may comprise an implant, to an instrument for implantation of the latter and to a method for manufacturing this implant which includes an elongated body between a free end and a head along a longitudinal axis on the one hand and turns of at least one threading on at least one portion of said body in proximity to the free end, along the longitudinal axis on the other hand, characterized in that the body includes a longitudinal internal conduit in at least one portion along the longitudinal axis, obtained by at least one first central machining operation parallel to the longitudinal axis and at least one second machining operation in a so-called transverse plane, not parallel to the longitudinal axis and crossing the wall of the body as far as the longitudinal internal conduit by making windows communicating between said longitudinal internal conduit and the outside of the body while preserving at least one portion of said turns and the
(Continued)

wall of the body behind the turns, and preserving non-machined portions on the perimeter of said body.

6 Claims, 28 Drawing Sheets

(51) Int. Cl.
    *A61F 2/08*     (2006.01)
    *A61B 17/70*     (2006.01)
    *A61B 17/064*     (2006.01)

(52) U.S. Cl.
    CPC ...... *A61B 17/8605* (2013.01); *A61B 17/8625* (2013.01); *A61B 17/0642* (2013.01)

(56) References Cited

U.S. PATENT DOCUMENTS

| | | |
|---|---|---|
| 2010/0280555 A1 | 11/2010 | Aflatoon et al. |
| 2012/0010662 A1 | 1/2012 | O'neil et al. |
| 2017/0224393 A1 | 8/2017 | Lavigne et al. |

FOREIGN PATENT DOCUMENTS

| | | |
|---|---|---|
| EP | 3185791 A1 | 7/2017 |
| FR | 2954692 A1 | 7/2011 |
| WO | WO-2016016474 A1 | 2/2016 |

OTHER PUBLICATIONS

"European Application Serial No. 15756357.8, Response filed Sep. 20, 2017 to Communication pursuant to Rules 161(1) and 162 EPC dated Mar. 10, 2017", 12 pgs.

"International Application Serial No. PCT/EP2015/067861, International Preliminary Report on Patentability dated Feb. 16, 2017", 9 pgs.

"International Application Serial No. PCT/EP2015/067861, International Search Report dated Nov. 12, 2015", w/ English Translation, 7 pgs.

"International Application Serial No. PCT/EP2015/067861, Written Opinion dated Nov. 12, 2015", w/ English Translation, 13 pgs.

U.S. Appl. No. 15/501,166, filed Feb. 1, 2017, Bone Implants.

\* cited by examiner

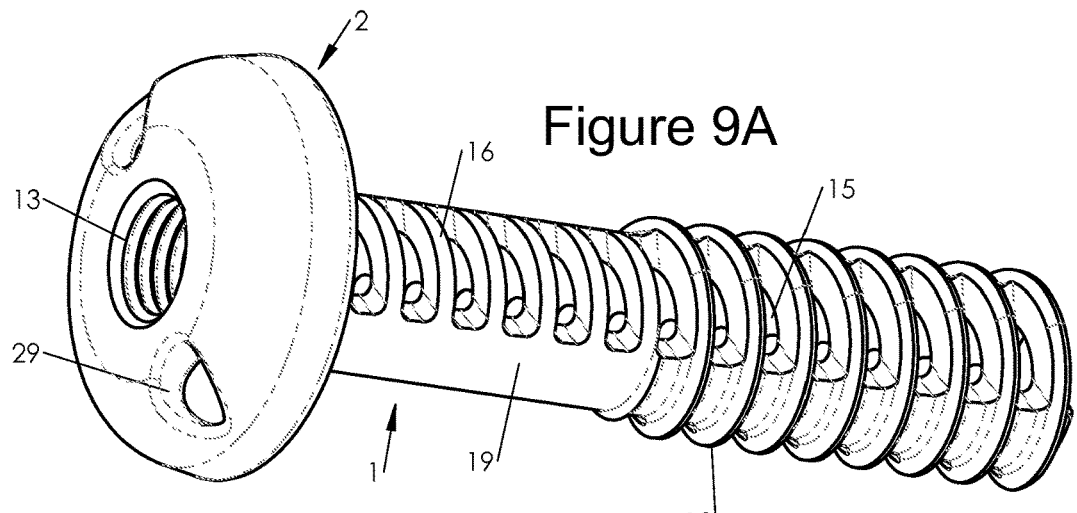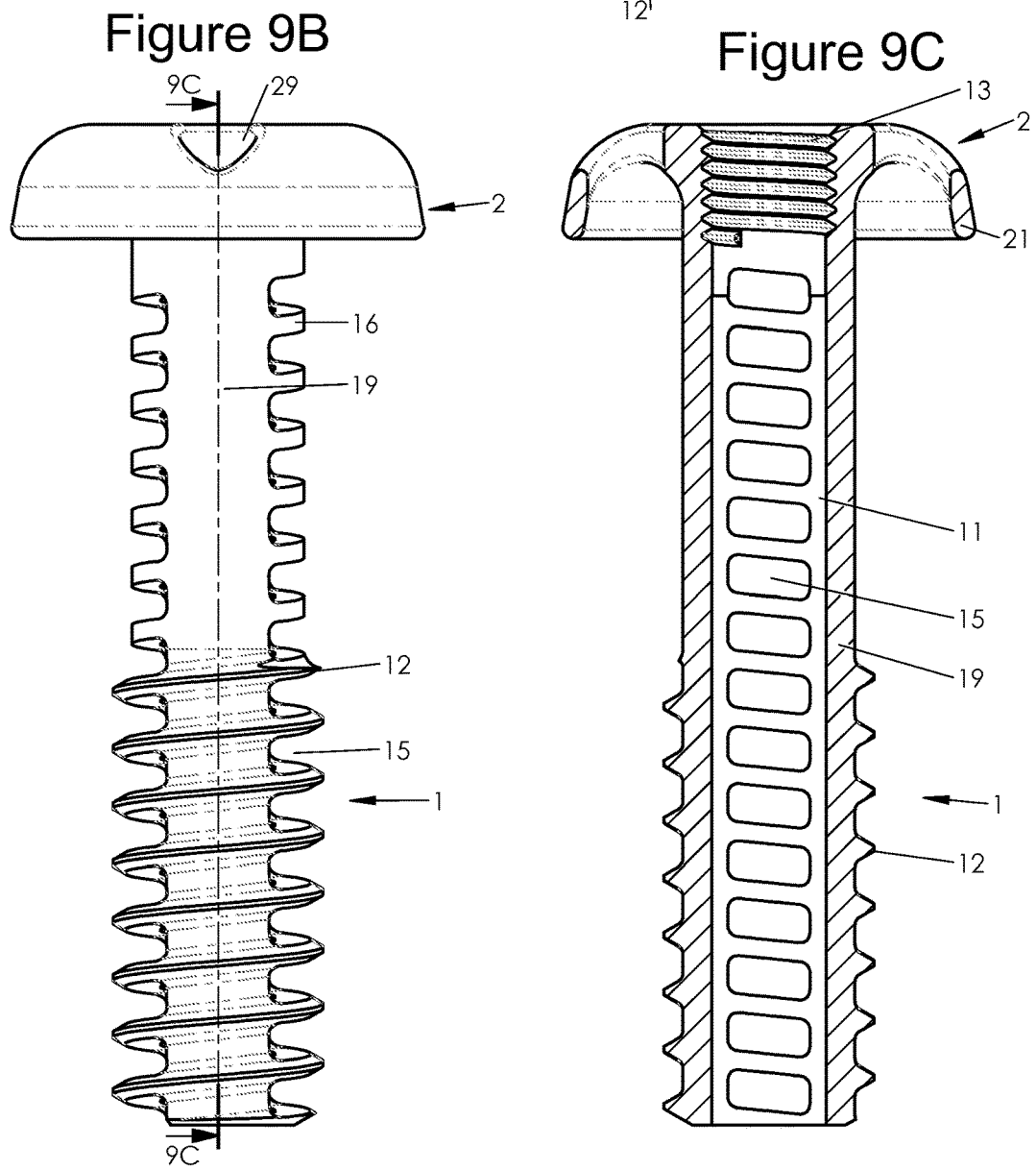

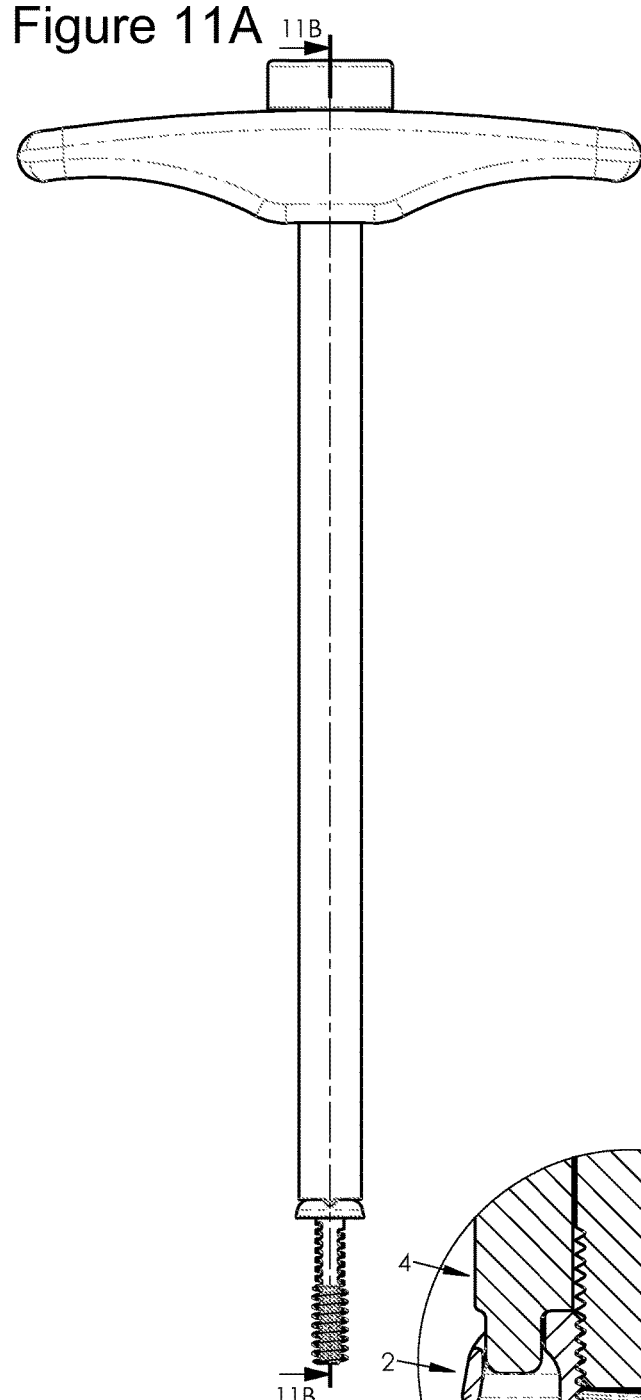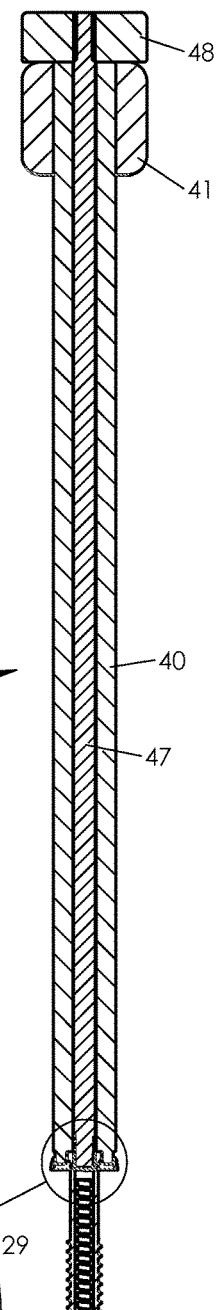
Figure 11A
Figure 11B
Figure 11C

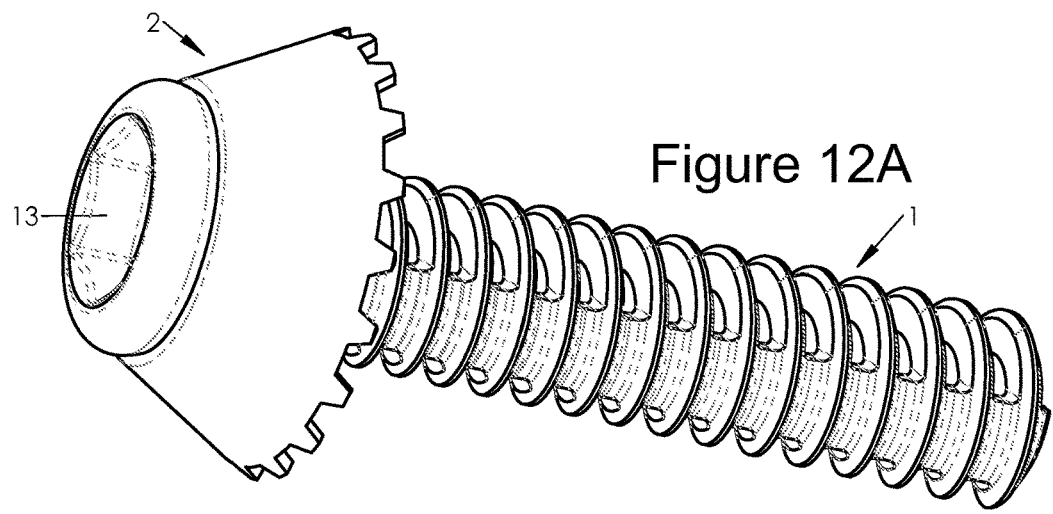
Figure 12A
Figure 12B
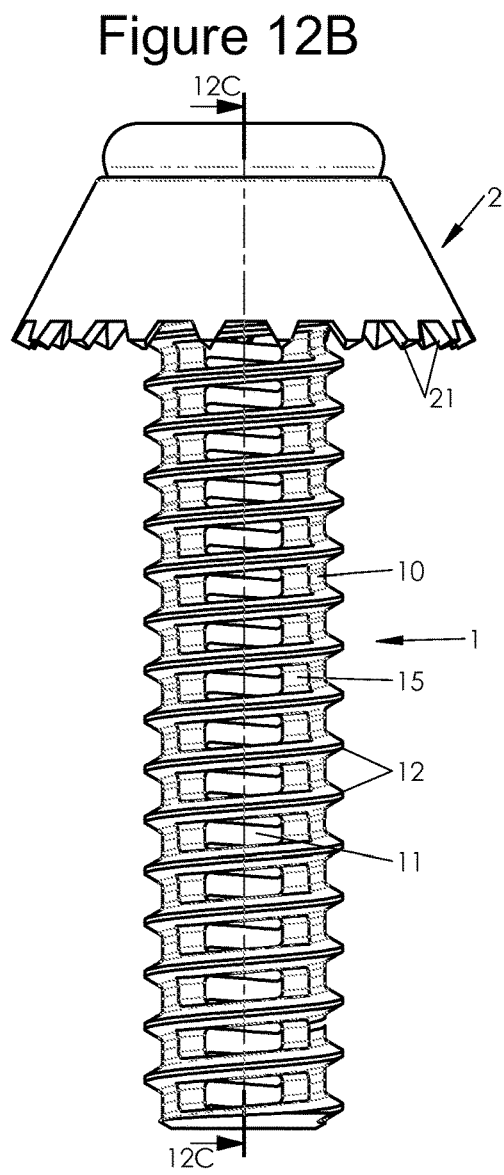
Figure 12C
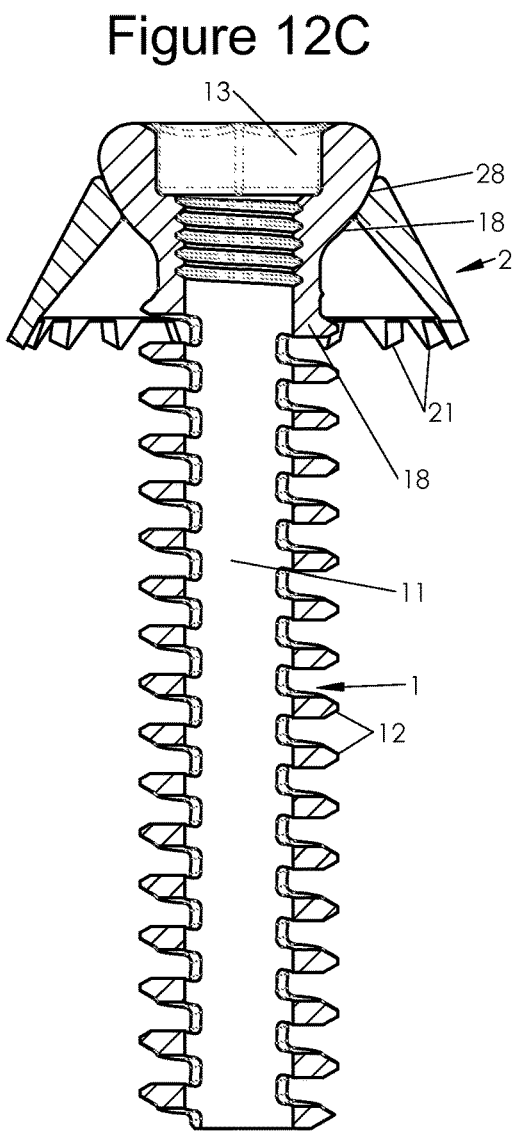

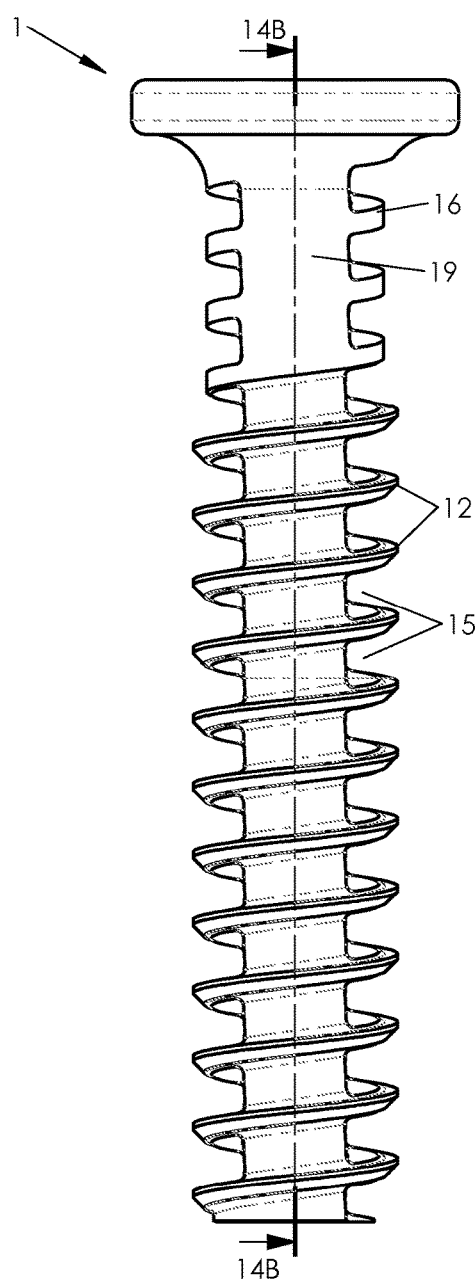
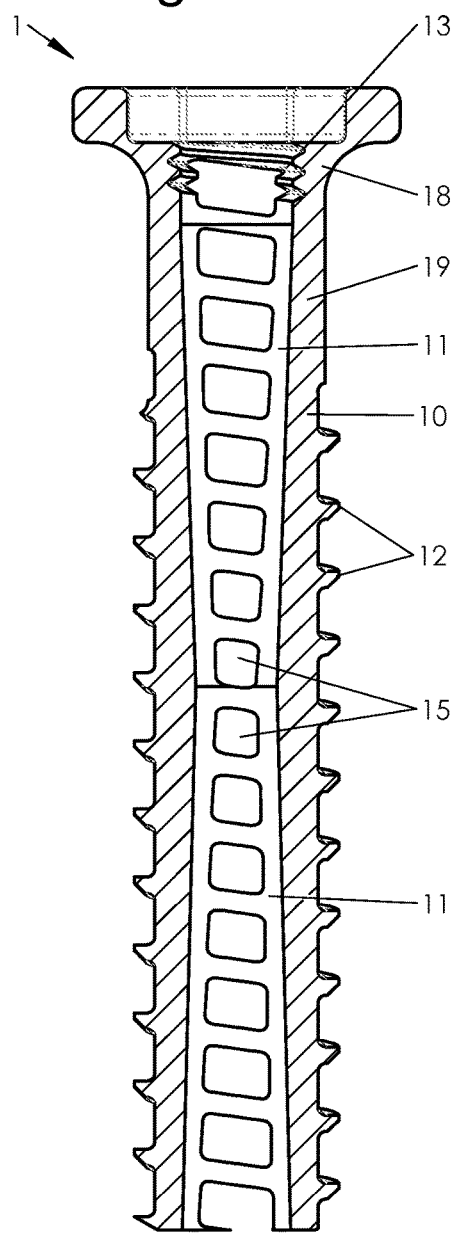
Figure 14A
Figure 14B

Figure 15A
Figure 15B
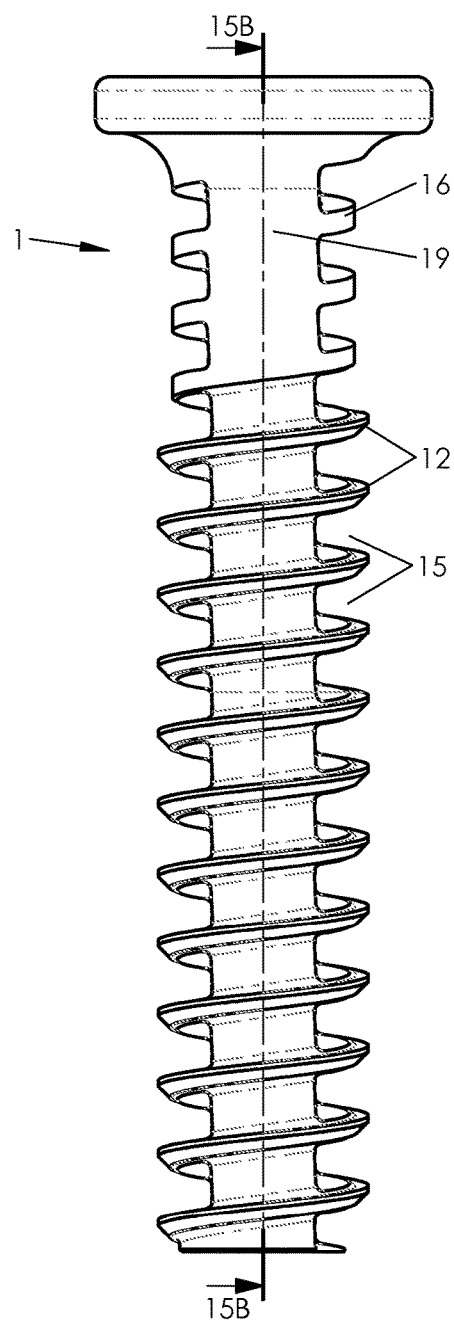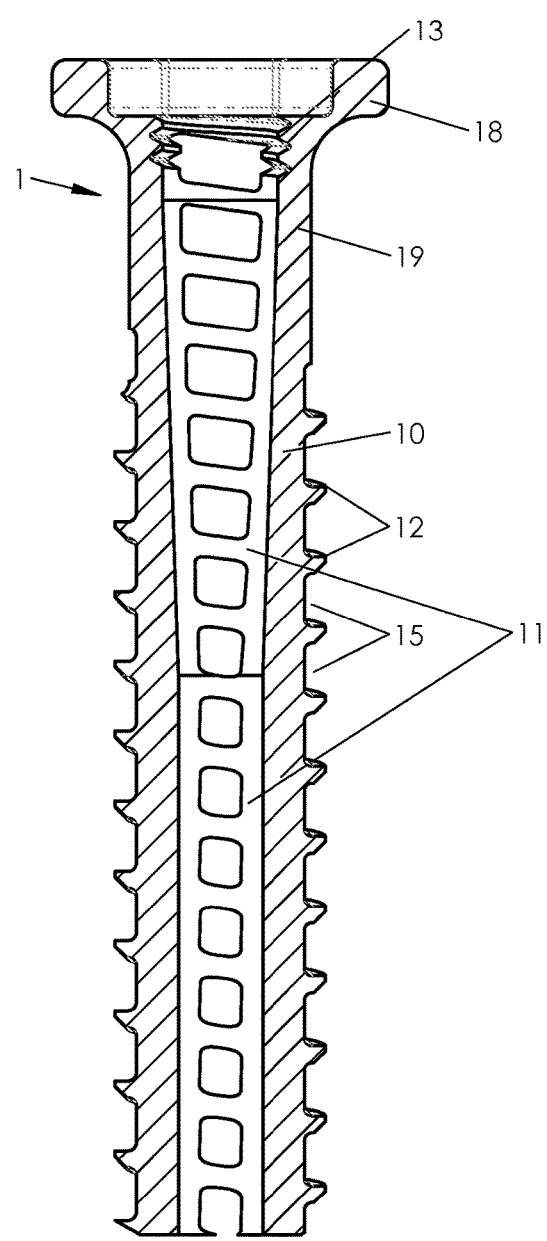

Figure 16A
Figure 16B
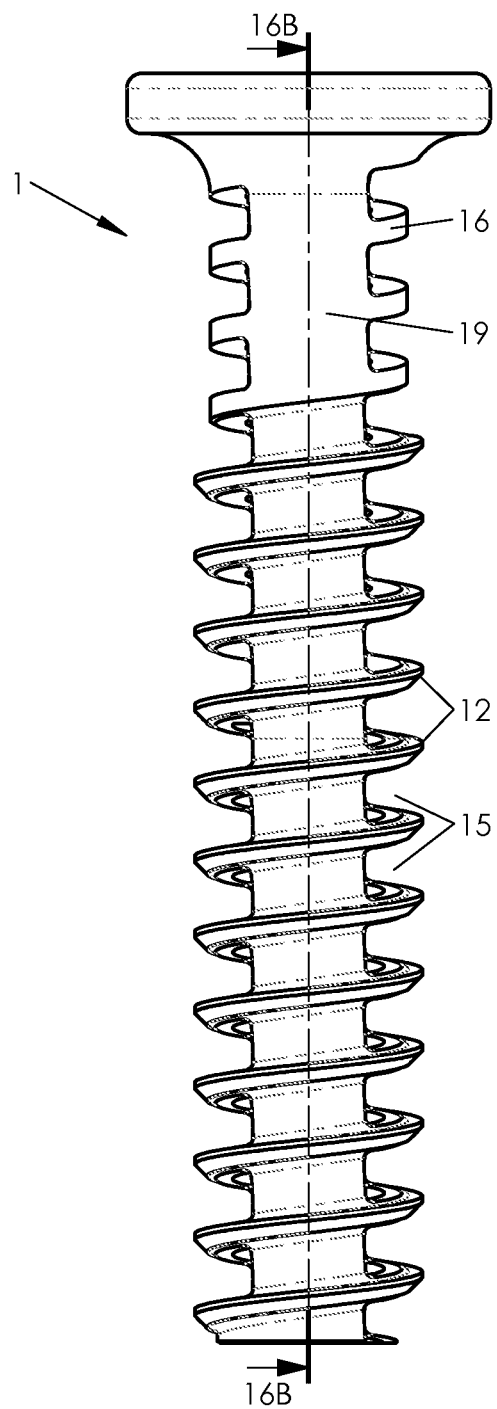
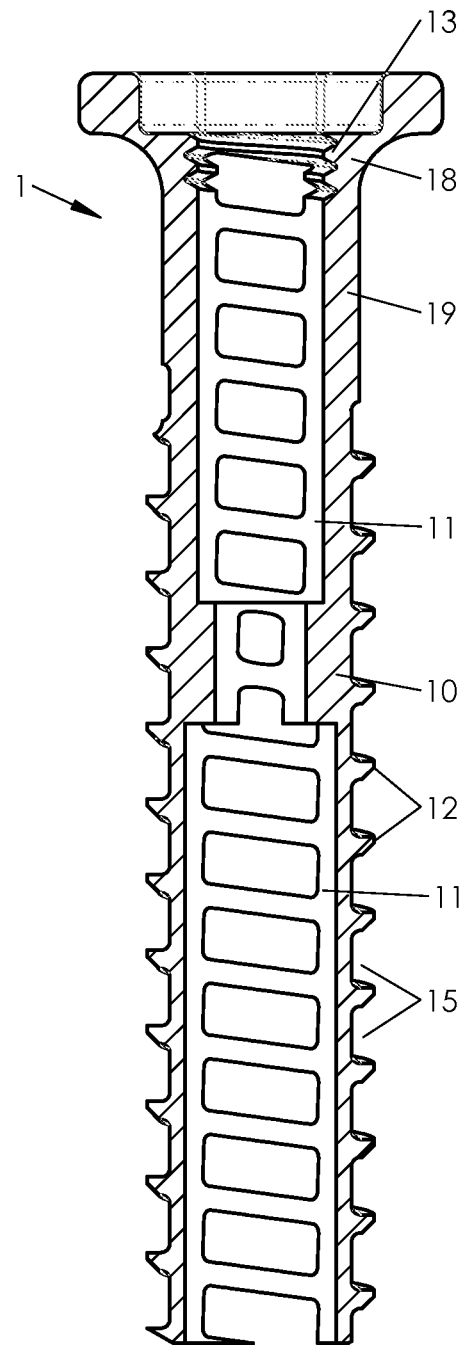

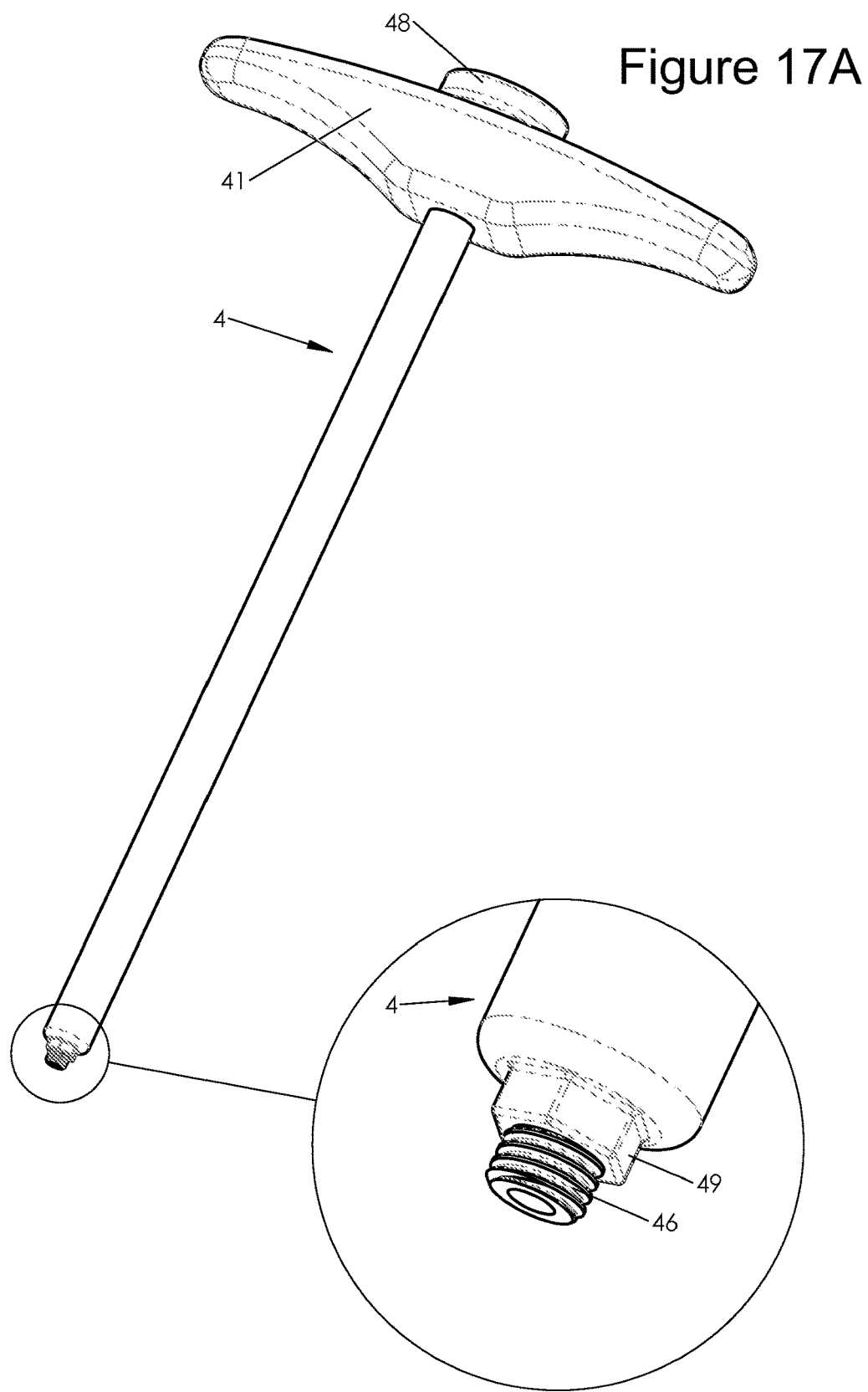

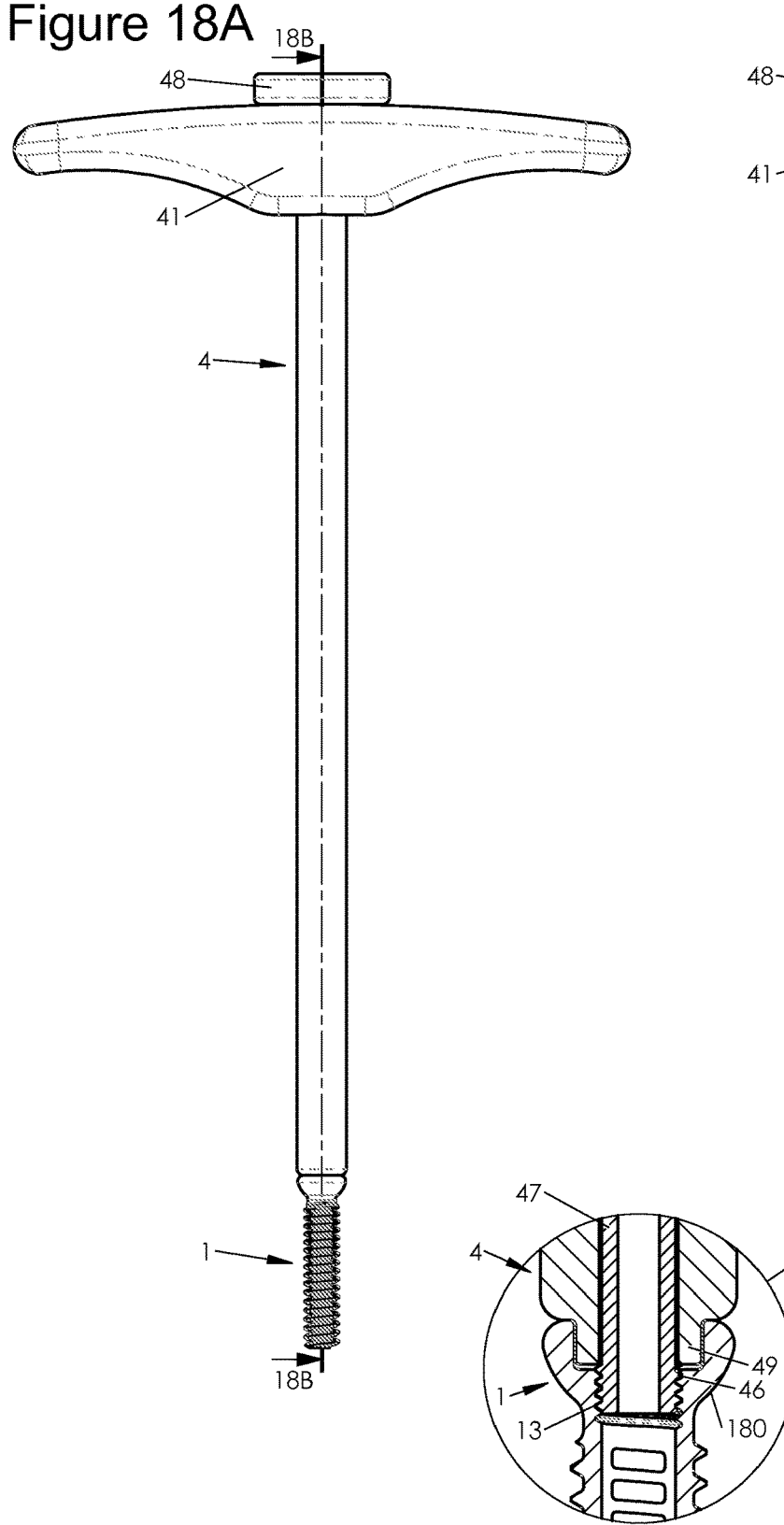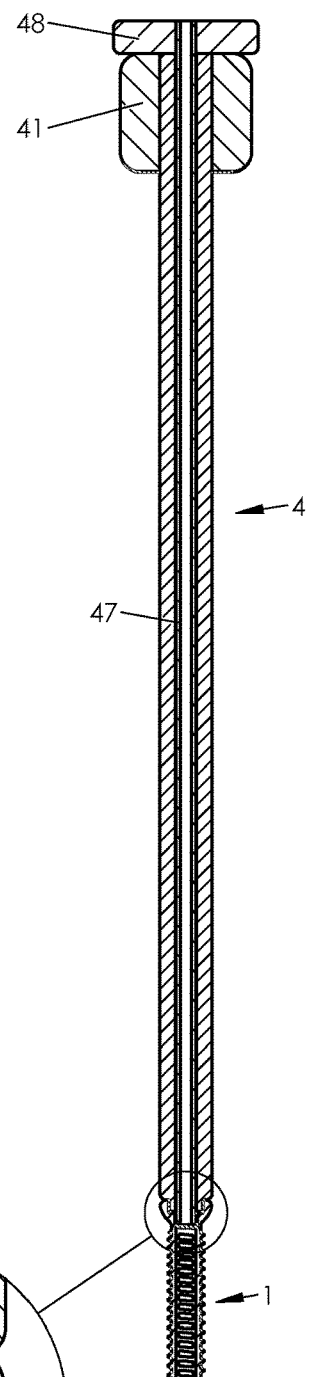
Figure 18A
Figure 18B
Figure 18C

Figure 20A
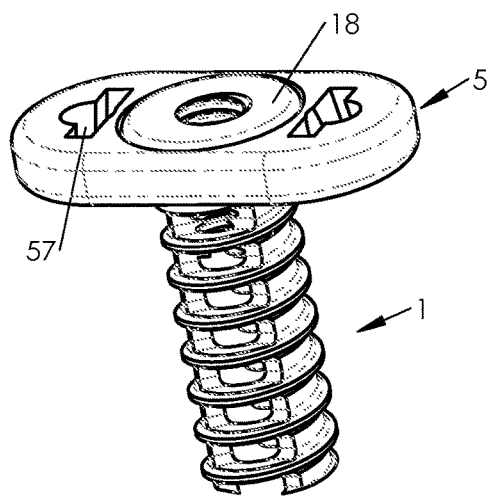
Figure 20B
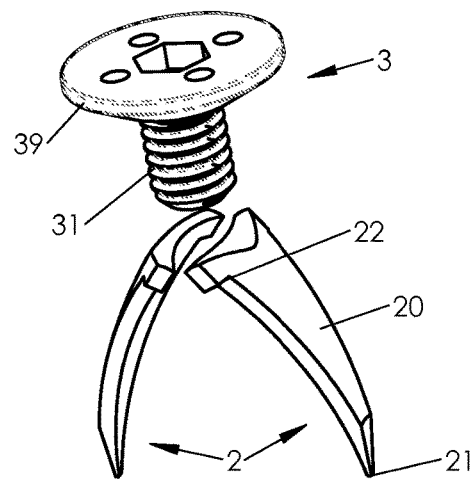
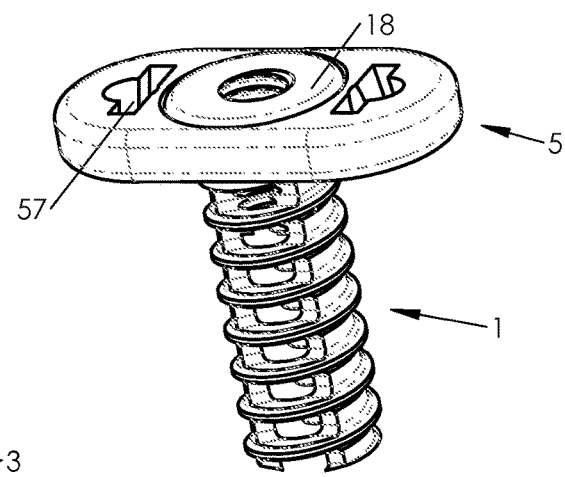
Figure 20C
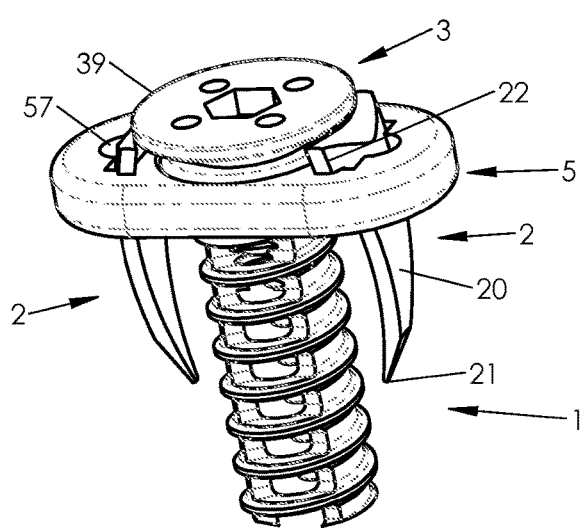

Figure 24A
Figure 24B
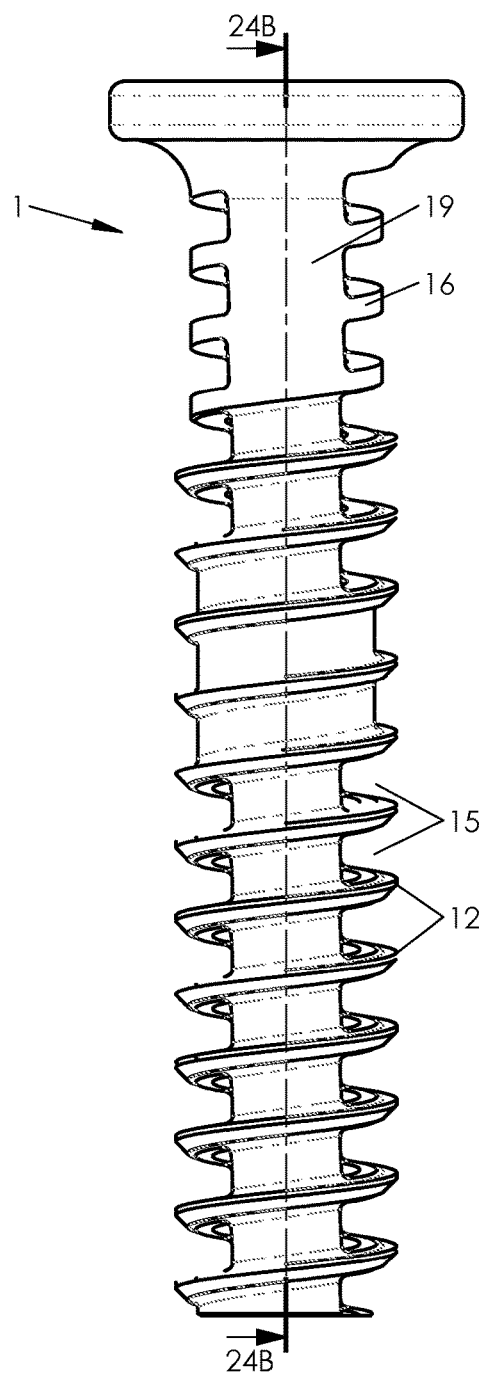
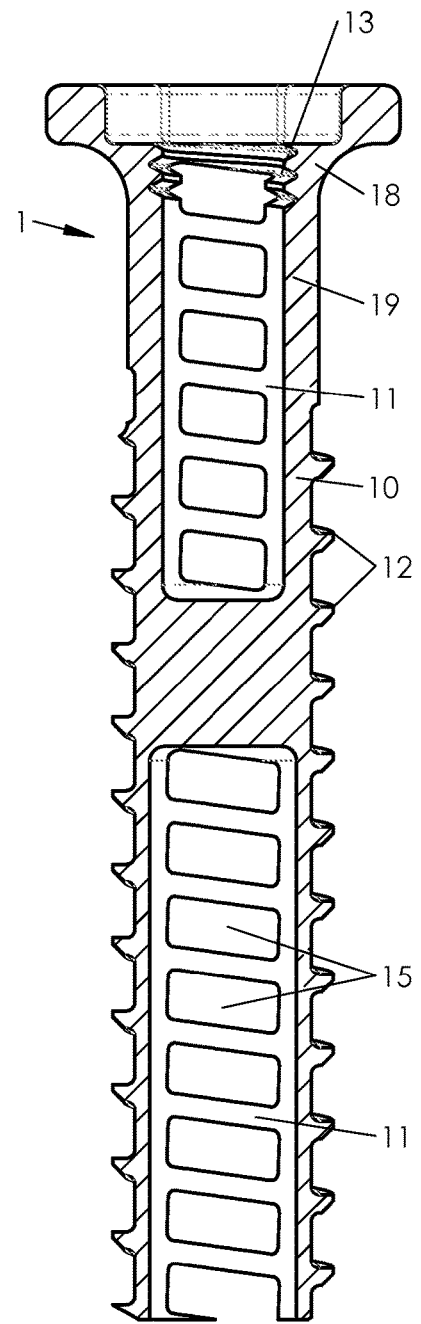

Figure 28A
Figure 28B
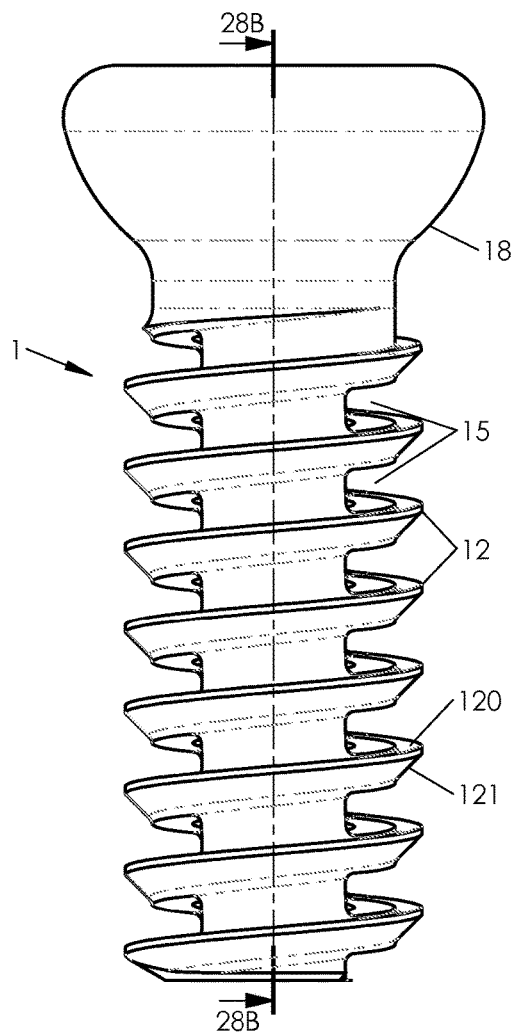
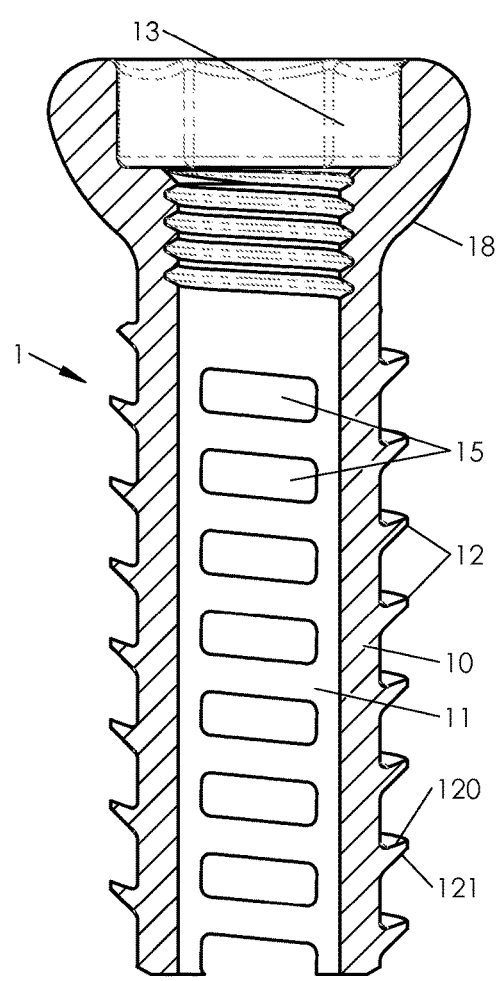

BONE IMPLANTS

CROSS-REFERENCE TO RELATED APPLICATIONS

This application claims priority under 35 U.S.C. § 119 to French patent application number FR1457539 filed in France on Aug. 1, 2014, which is incorporated herein by reference.

BACKGROUND

This disclosure relates to the field of bone implants, in particular spinal implants, for example for arthrodesis of the two vertebral structures. This disclosure more particularly relates to spinal implants, notably so called "facet" implants intended to be implanted between the articular facets of the vertebrae (so-called "intra-facet" implants) and/or implanted through these articular facets of the vertebrae (so-called "trans-facet" implants). Various embodiments of the present application may be also adapted to implantation in vertebral pedicles (so-called "pedicular" implants) or at the sacro-iliac joint or in various types of bone structures, either spinal or not, although the characteristics of the implants described in the present application make them particularly useful for their use in the rachis A problem in the field of implants relates to bone growth and notably arthrodesis, i.e. the bone merging of two structures, such as for example vertebrae. Indeed, it is sometimes sought to obtain merging of at least two vertebrae for example when at least one of their adjacent intervertebral discs is lesioned. Various arthrodesis techniques are known from the prior art, based on various types of implants such as for example intersomatic cages (or arthrodesis cages) inserted in the place of a disc in order to promote bone growth, or arthrodesis plates attached on both vertebrae in order to immobilize them and allow arthrodesis, or further osteosynthesis or arthrodesis rods, used for immobilizing the vertebrae, to which they are generally connected through pedicular screws or hooks, or finally inter-spinal implants inserted between the spines of the vertebrae (or "spineous apophyses") for immobilizing them and thereby facilitating merging. These types of implants aim at finding an answer to a problem known in the field which is to stabilize the vertebral level to be treated. Solutions are also known, notably at the lumbar and sacral level, using facet implants allowing such stabilization, by attaching the articular facets with the purpose of obtaining merging. For example, implants are known from the prior art, such as for example from patent FR2726171B1, in the form of a hollow cylinder provided with threading for screwing bones, forming a screw in which a conduit and grooves are made in order to provide a grafting space allowing the insertion of tissue or bone substitute or cement for facilitating the merging of the structures in which the screw is implanted. It will be noted that vertebral articular apophyses (or articular processes or pedicular facets) are designated here by the term of "articular facet", since each vertebra is jointed with the one above and below through articular facets which are posterior and various embodiments may be useful for treating these articular facets, but it is possible to optionally use various embodiments on other structures, notably vertebral structures, such as for example costal or sacro-illiac facets if need be. Articular apophyses protrude above and below the base of transverse apophyses of the vertebrae, behind the pedicles. At the lumbar level for example, the upper articular apophyses are separated from each other by a more considerable distance than that which separates the lower two. The articular facets which they support have the shape of a vertical gutter, the concavity of which faces rearwards and inwards, a gutter in which may be placed the lower articular apophyses, which have a convex articular surface in the opposite direction, i.e. forwards and outwards. The lower articular apophyses provide a convex articular surface in the form of a cylinder segment, which faces outwards and slightly forwards. This surface slides in the concavity of the upper articular apophysis of the vertebra located below. These structures are therefore important for the stability of the vertebrae one on the other and it will moreover be noted that the bone deficit (or "lysis") of the isthmuses (or "pars interarticularis") located at their base is often responsible for spondilolysthesis (the sliding of a vertebra relatively to the other adjacent ones) which generally lead to degeneration of intervertebral discs. When it is sought to achieve vertebral arthrodesis, it is therefore sometimes desirable to use a facet implant for attaching the lower articular apophyses of a vertebra to the upper articular apophyses of the adjacent vertebra. These facet implants may either be "inter-facet" implants, i.e., they are inserted between the articular surfaces, or "trans-facet" implants, i.e. they are inserted through the articular apophyses for attaching the articular surfaces together. Inter-facet implants are generally set into place in the articular joint by identifying the approach axis and for example by positioning a broach used as a guide for the implant, which is often cannulated (i.e. hollow). A problem in the field relates to the solidity since it is desirable to guarantee the integrity of the implant in spite of its small size and its often recessed layout.

A problem relating to implants in general, in particular spinal implants and notably facet implants, relates to the stability of the implant. It is required that an implant be stable in its implantation site, in particular when arthrodesis is desired since the latter should take place in a relative position of the elements of the rachis, which is optimum. Stabilization and/or locking of the implant is(are) therefore often preferable. Another general problem relates to the ease and/or the rapidity of the implantation. Further, it is generally desired that the implants may be implanted with minimum invasiveness, i.e. it is sought to limit the size of the incisions and of the damages on the surrounding tissues. Percutaneous solutions or only requiring a few millimeters of incision (for example 2 to 40 mm) are often sought. Further, it is generally desirable to limit resorting to imaging in order to avoid exposing the patients to rays.

Intra-facet implants, often accompanied by other problems such that, for example, the requirement of providing the graft or bone substitute or cement for facilitating the merging, for example by means of the presence of a grafting chamber in the implant, in spite of its small size, and by maintaining sufficient rigidity of the implant in order to support the forces between both fixed facets. Further, it is generally desirable to tap, clean out or sharpen the articular surfaces, for example in order to remove cartilage and/or promote bone growth.

Transfacet implants, which often provide the advantages of being simple, being able to be used percutaneously and allowing compression of articular facets against each other, are often accompanied by other problems such as for example, the lack of sharpening, cleaning or tapping of the articular joints, which limits the bone growth rate. These implants generally include at least one implanted screw with an aim through articular surfaces (transfacet). They are generally also guided by a broach but they generally require that the bone be perforated beforehand, often percutaneously by means of a bit. It is possible to tap the bone around the broach in order to screw in the implant (often "cannulated", i.e. hollow and slipped around the broach) which generally includes a bone thread (e.g., a threading adapted for screwing into bone tissue), for example for not risking any fracturing of the facets during the setting into place. Finally, it is generally desirable that these implants include a stabilization means (of either one of the facet or both facets) and/or a compression and/or locking means and/or bone supporting means which may spread the loads over at least one of the facets (notably the posterior facet) at the end of the screwing.

The diversity of the problems, notably of those discussed above, is generally accompanied by the problem that a same implant cannot be equally used as a transfacet implant and as an interfacet implant, which forces the provision of various types of implants and instruments.

In this context, it is interesting to propose a solution with which it is possible to efficiently provide an answer to said at least one portion of these problems.

The object of various embodiments of this disclosure is to overcome various drawbacks of the prior art by proposing a bone implant, in particular intended for implantation at articular facets, further allowing stable, easy and rapid implantation.

BRIEF SUMMARY OF VARIOUS ASPECTS OF THE DISCLOSURE

The present disclosure provides various embodiments that may comprise an implant, to an instrument for implantation of the latter and to a method for manufacturing this implant which includes an elongated body between a free end and a head along a longitudinal axis on the one hand and turns of at least one threading on at least one portion of said body in proximity to the free end, along the longitudinal axis on the other hand, characterized in that the body includes a longitudinal internal conduit in at least one portion along the longitudinal axis, obtained by at least one first central machining operation parallel to the longitudinal axis and at least one second machining operation in a so-called transverse plane, not parallel to the longitudinal axis and crossing the wall of the body as far as the longitudinal internal conduit by making windows communicating between said longitudinal internal conduit and the outside of the body while preserving at least one portion of said turns and the wall of the body behind the turns, and preserving non-machined portions on the perimeter of said body.

BRIEF DESCRIPTION OF THE SEVERAL VIEWS OF THE DRAWING

Other particularities and advantages of the various disclosed embodiments will become more clearly apparent upon reading the description hereafter, made with reference to the appended drawings, wherein:

FIGS. 9A and 9B illustrate perspective and profile views respectively of an implant according to various embodiments and FIG. 9C illustrate a sectional view along a sectional plane 9C-9C of FIG. 9B, FIGS. 11A and 11B illustrate profile and sectional views respectively, along the sectional plane 11B-11B of FIG. 11A of an implant-holder retaining an implant according to various embodiments and FIG. 11C illustrates an enlargement of FIG. 11B, FIGS. 12A and 12B illustrate perspective and profile views respectively of an implant according to various embodiments and FIG. 12C illustrates a sectional view along the sectional plane 12C-12C of FIG. 12B, FIGS. 13A and 13B illustrate profile and sectional views, respectively, along the sectional plane 13B-13B of FIG. 13A, of an implant according to various embodiments, FIGS. 14A and 14B illustrate profile and sectional views, respectively, along the sectional plane 14B-14B of FIG. 14A of an implant according to various embodiments, FIGS. 15A and 15B illustrate profile and sectional views, respectively along the sectional plane 15B-15B of FIG. 15A, of an implant according to various embodiments, FIGS. 16A and 16B illustrate profile and sectional views, respectively, along the sectional plane 16B-16B of FIG. 16A, of an implant according to various embodiments, FIG. 17A illustrate a perspective view of an implant-holder according to various embodiments and FIG. 17B illustrates an enlargement of this implant-holder at its portion indented to retain the implant, FIGS. 18A and 18B represent profile and sectional views, respectively, along the sectional plane 18B-18B of FIG. 18A, of an implant-holder retaining an implant according to various embodiments and FIG. 18C illustrates an enlargement of FIG. 18B, FIGS. 19A and 19B illustrate perspective views of stabilization means before and after assembling respectively, according to various embodiments FIG. 20A, illustrates a perspective view of an implant and of a portion of stabilization means according to various embodiments and FIGS. 20B and 20C illustrate perspective views of an implant provided with stabilization means and locking means, before and after assembling respectively, according to various embodiments, FIGS. 28A and 28B illustrate profile and sectional views, respectively, along the sectional plane 28B-28B of FIG. 28A, of an implant according to various embodiments.

DESCRIPTION OF VARIOUS EMBODIMENTS

Figure 1A:
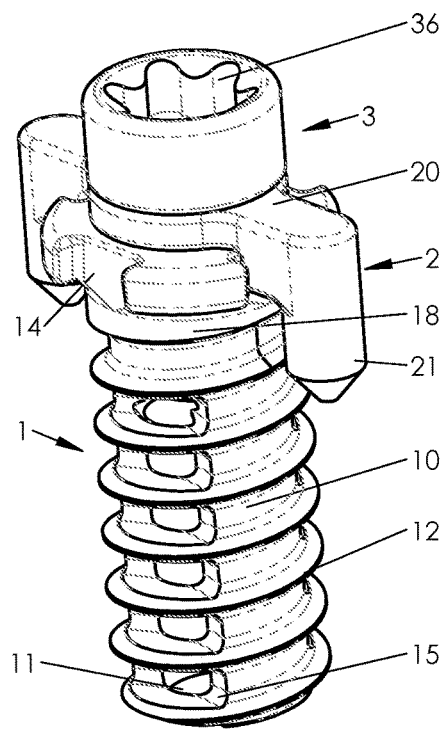
FIGS. 1A, 1B and 1C represent respective, front and profile views, respectively of an implant according to various embodiments.
Figure 1B:
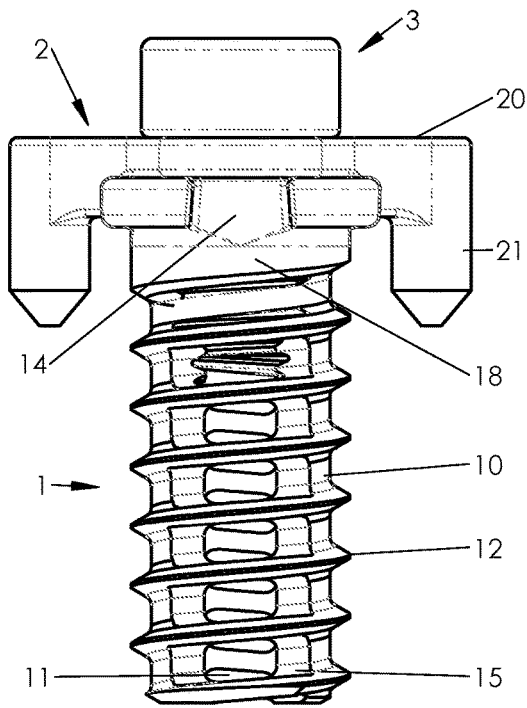

The present disclosure relates to various embodiments of bone implants and of instruments for implanting such implants. As mentioned in the preamble of the present application, various embodiments may relate in particular to spinal implants, for example for arthrodesis of two vertebral structures. The present application more particularly details spinal implants, notably so-called "facet" implants, intended to be implanted between the articular facets of the vertebrae (so-called "intra-facet" implants) and/or implanted through these articular facets of the vertebrae (so-called "trans-facet" implants). Various embodiments of the present application may be also adapted to an implantation in vertebral pedicles (so called "pedicular" implants) or at the level of the sacro-illiac joint or in various types of bone structures, either spinal or not, although the characteristics of the implants described in the present application make them particularly useful for their use in the rachis. Further, the implants of various embodiments may be obtained by a manufacturing method with which it may be possible to obtain particularly useful implants, for example for providing at least an answer to part of the problem discussed in the present applications. Thus, various embodiments may also relate to the method for manufacturing these implants.

Generally, the many configurations of embodiments preferably may include at least one bone implant (1), the technical characteristics of which are detailed hereafter in various embodiments. Generally, in the case of an implantation at articular facets, it may be preferred to use two implants so as to secure the two (left and right) facets which joint two adjacent vertebrae, but this use is of course not limiting.

Generally, the bone implant (1) may include a body (10) elongated between a free end and a head (18) along a longitudinal axis on the one hand and, turns (12) of at least one threading, on at least one portion of said body (10) in proximity to the free end, along the longitudinal axis on the other hand. Further, the body (10) of the implant (1) preferably may include at least one longitudinal internal conduit (11) on at least one portion of a body (10) along the longitudinal axis and windows (15) in communication between said longitudinal internal conduit (11) and the outside of the body (10).

Figure 22A:
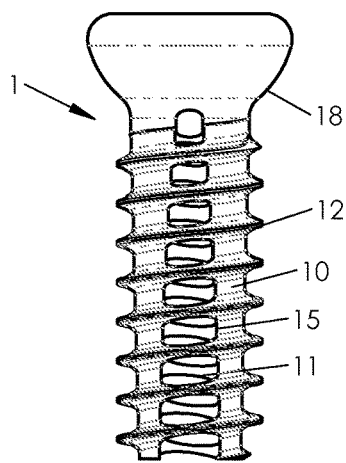
FIGS. 22A, 22B and 22C illustrate front, profile and top views, respectively, of an implant according to various embodiments.
Figure 22B:
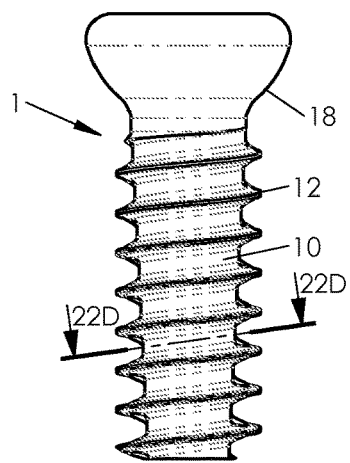
Figure 22C:
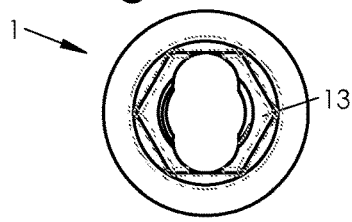
Figure 22D:
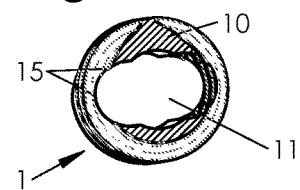
FIG. 22D illustrates a sectional view along the sectional plane 22D-22D of FIG. 22B, FIGS. 22E, 22F and 22G illustrate front, profile and top views, respectively, of an implant according to various embodiments.
Figure 22E:
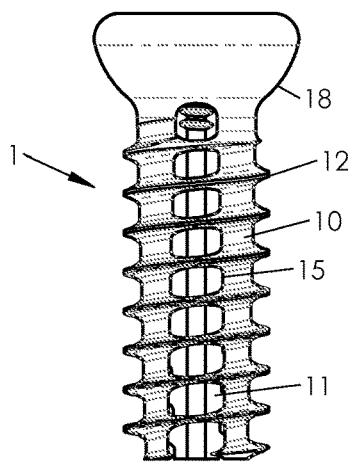
FIG. 22H illustrates a sectional view along the sectional plane 22H-22H of FIG. 22F, FIGS. 23A, 23B, 23C and 23E illustrate front, profile, top and perspective views, respectively, of an implant according to various embodiments.
Figure 22F:
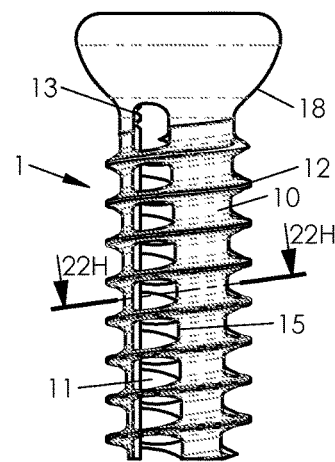
Figure 22G:
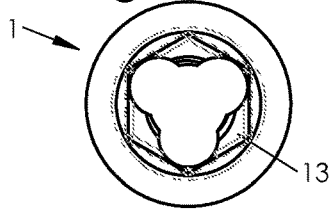
Figure 22H:
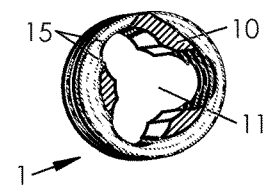

In certain embodiments, this longitudinal internal conduit (11) may be obtained by at least one first central machining operation parallel to the longitudinal axis and at least one second machining operation in a so-called transverse plane, not parallel to the longitudinal axis and crossing the walls of the body (10) as far as the longitudinal internal conduit (11) by making windows (15) in communication between said longitudinal internal conduit (11) and the outside of the body (10). Thus, the implant may include an internal conduit (11) which preserves at least one portion of said turns (12) and the wall of the body behind the turns, and preserves non-machines portions thereof on the perimeter of said body (10). Generally, regardless of how the internal conduit (11) is obtained, such non-machined portions on the perimeter of said body (10) may be preserved so as to improve the solidity of the implant. It is understood that it may be possible to preserve a variable number of non-machined portions depending on the number of transverse machining operations carried out. For example it may be possible to provide two diametrically opposite portions or three gradually distributed portions around the longitudinal axis (either regularly distributed or not) or further a multitude of portions for example as visible in FIG. 1C, 22F or 2D.

The terms of "head" and "free end" are used in the present disclosure with reference to the fact that the implant generally appears in the form of a screw, with a generally cylindrical or conical or frusto-conical body (10), but these turns and these shapes of the implant should not be considered as limiting. Diverse portions of the implant are on the other hand designated in the present application by the terms of "proximal" meaning "in proximity to the head", or "distal" meaning "in proximity to the free end" or further "median" meaning "substantially in the middle between the two ends", but it is clear that these terms are not either limiting and that the person skilled in the art will appreciate that the position of these portions may vary along the longitudinal axis. Further, the term of "appreciably" or "substantially" is used with reference to various features in order to indicate that they may be exactly as defined or be approximately as defined. For example, the expression "a substantially planar shape" should be understood as designating a shape approximately planar since the person skilled in the art will be able to vary the exact shape insofar that it would keep a globally planar shape meeting the relevant technical requirements. Also, the present description may define features without this specifying of approximation with the terms of "appreciably" or "substantially" but it will be clear for the person skilled in the art that this notion applies even in the absence of such terms.

Further the term of "machining" is here used in a non-limiting way for referring to the manufacturing of the implants and it is clear that this term in facts covers any type of manufacturing techniques, such as for example, bores, drillings or milling operations, but also electro-erosion or any type of technique giving the possibility of making surfaces or accommodations on or in the implants. Further the term of "transverse" is used for indicating that the second machining operation is in a plane not parallel to the longitudinal axis and tends to indicate that it may be perpendicular to the longitudinal axis, but the person skilled in the art will notably understand because of the oblique orientations of the turns of the threading, that this plane (which may be therefore substantially transverse) may be not necessarily perpendicular to the longitudinal axis and may generally be rather obliquely oriented, preferably parallel to the turns.

Figure 1C:
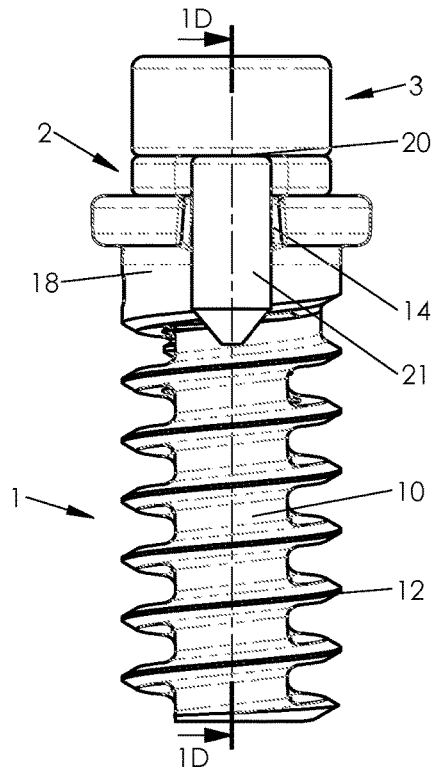
Figure 1D:
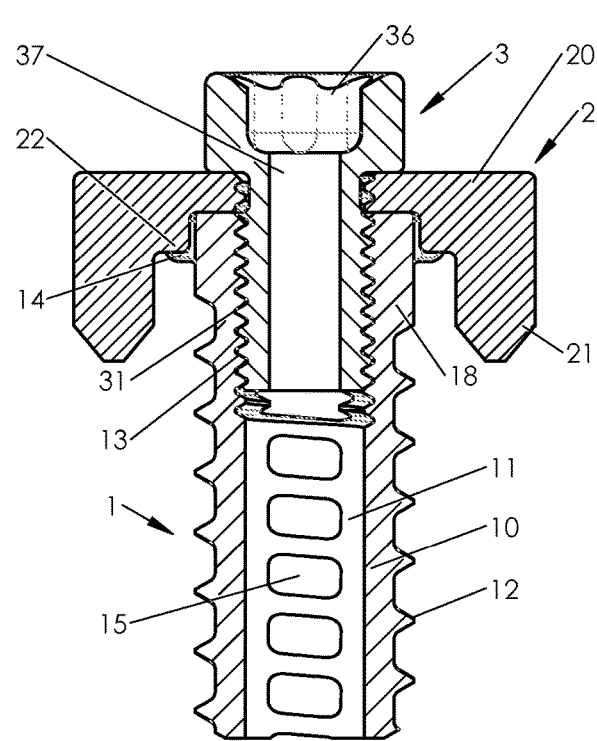
FIG. 1D illustrates a sectional view along the sectional plane 1D-1D of FIG. 1C, FIGS. 2A and 2D illustrate perspective views of an implant according to various embodiments
Figure 2A:
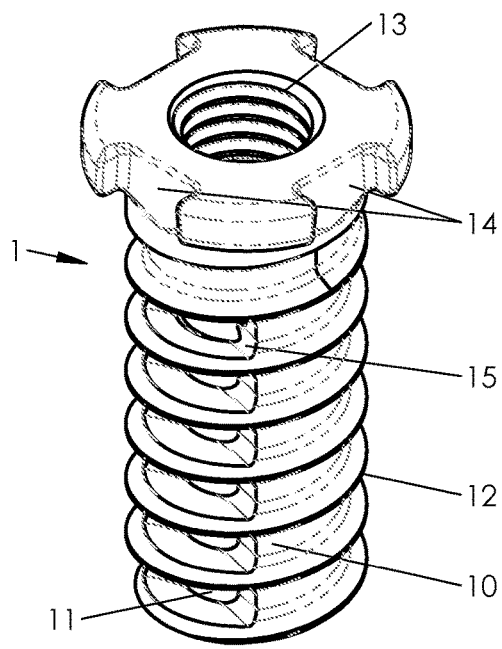
FIGS. 2B and 2C illustrate perspective views, of a locking means and of a stabilization element, respectively, according to various embodiments.
Figure 2B:
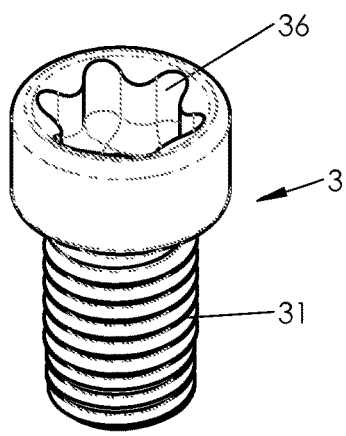
Figure 2C:
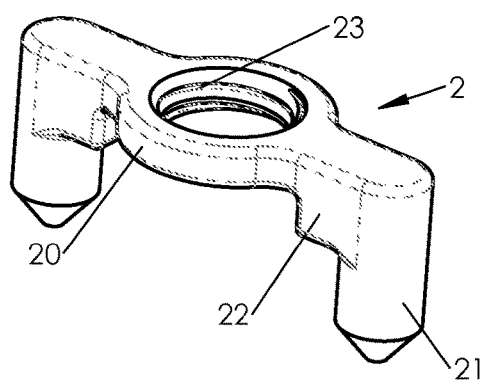
Figure 2D:
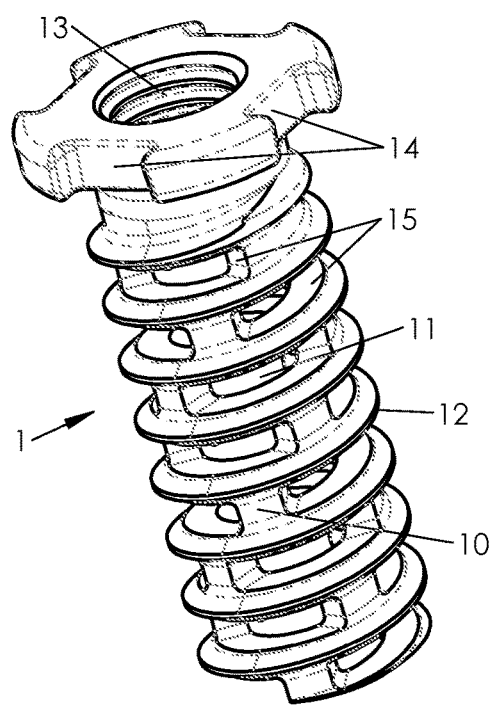

In certain embodiments, said body (10) may be substantially cylindrical, as for example visible in most of the figures, notably FIGS. 1C, 2D, 9C, etc. In other embodiments, said body (10) may be substantially conical or frusto-conical, as illustrated for example in FIG. 22A, 22B, 22E, 22F or 23A, 23B and 23E. This shape facilitates implantation of the body since the free (distal) may be thinner than the proximal end. In some of these embodiments with a conical or frusto-conical body, the perimeter of said threading may be substantially cylindrical in spite of the conical or frusto-conical shape of the body (10), as for example illustrated in FIGS. 22A, 22B, 22E and 22F. This type of threading with a cylindrical perimeter on a frusto-conical body improves the stability of the implant since the turns of the distal end may penetrate more deeply into the bone tissue.

Regardless of how the windows are obtained (longitudinal or transverse machining operations), aligning them or shifting them relatively to each other may be preferred. Thus, in certain embodiment, said windows (15) may be shifted relatively to each other along (or around) the longitudinal axis, for example as illustrated in FIG. 2D, while in other embodiments, said windows (15) may be aligned with each other along the longitudinal axis, for example as illustrated in FIG. 1C. It will be noted that it may be also possible to provide a combination of these arrangements, by providing aligned windows on one portion and shifted windows on another portion. When they are shifted relatively to each other, it may be generally preferred that a more proximal window be shifted relatively to a more distal window on the side which corresponds to the direction of the screwing. Thus, for example with a threading oriented clockwise a proximal window may be shifted left relatively to a more distal window, so as to improve sharpening of the bone or cartilage which may be gradually obtained with successive windows during screwing.

Figure 26A:
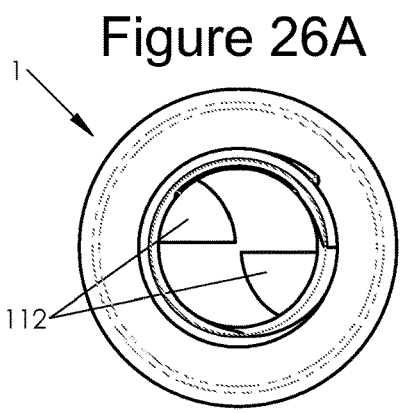
FIGS. 26A, 26B and 26C illustrate top, profile and sectional views, respectively, along the sectional plane 26C-26C of FIG. 26B, of an implant according to various embodiments.
Figure 26B:
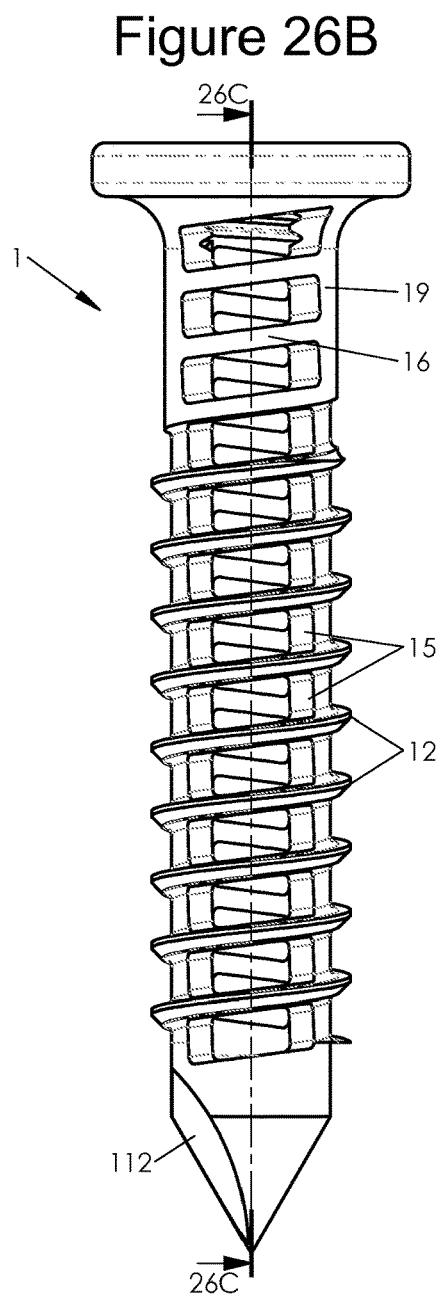
Figure 26C:
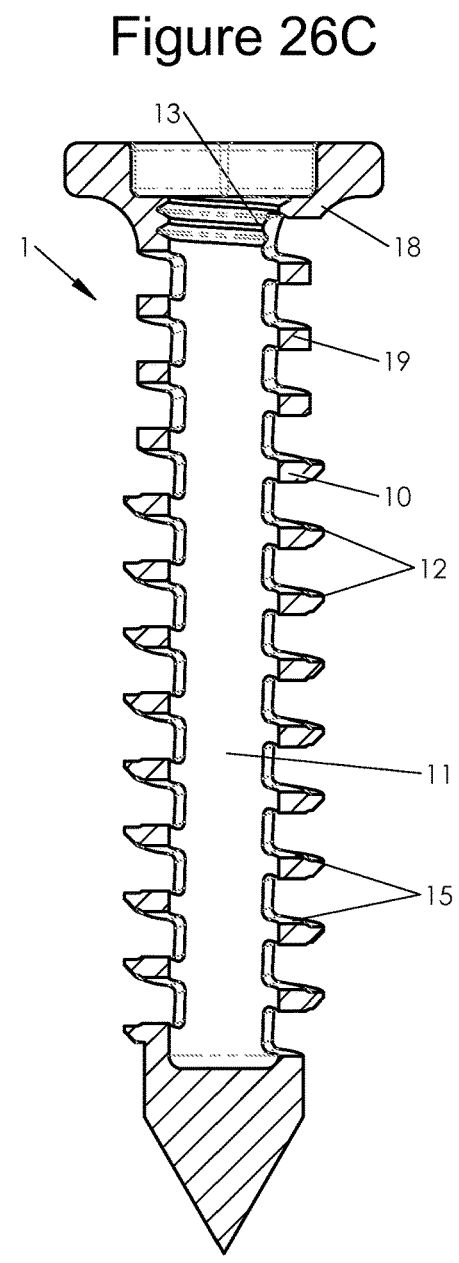
Figure 27A:
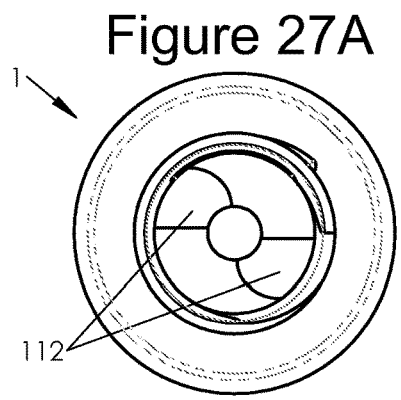
FIGS. 27A, 27B and 27C illustrate top, profile and sectional views, respectively, along the sectional plane 27C-27C of FIG. 27B, of an implant according to various embodiments.
Figure 27B:
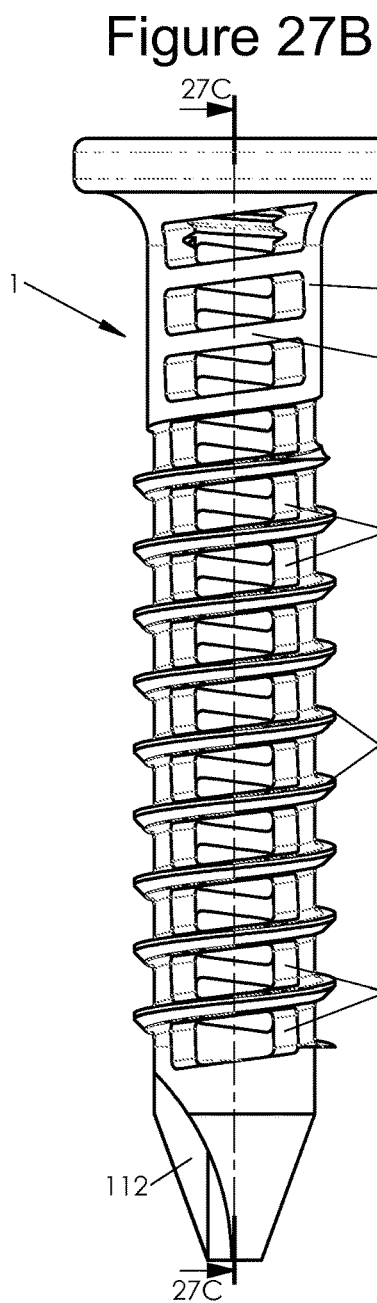
Figure 27C:
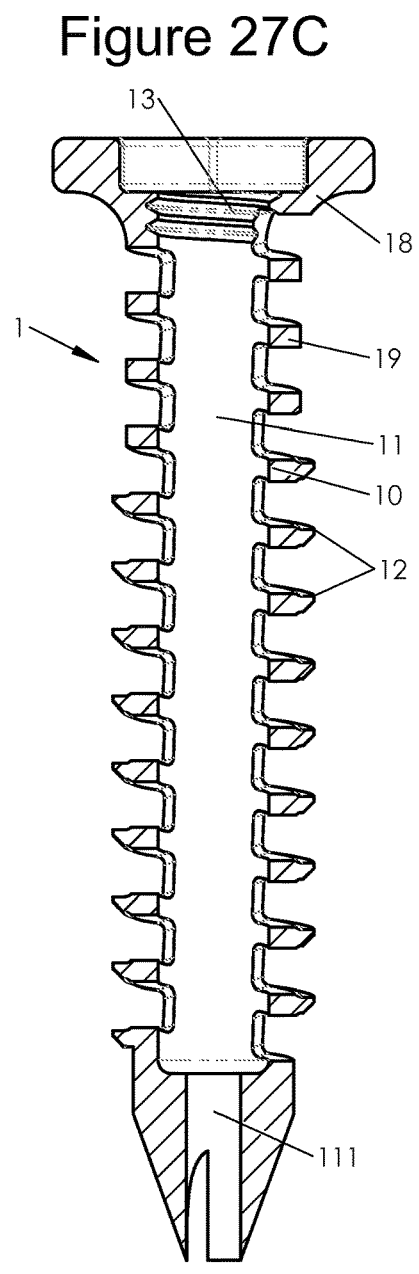

In various embodiments comprising a longitudinal internal conduit (11) and windows (15) obtained by at least one first machining operation and at least one second machining operation respectively, the second machining operation may preserve the material of the body (10) behind the turns (12) as illustrated for example in FIGS. 1C, 1D, 2D, 7C and more particularly visible in FIG. 12C, 26C or 27C. Thus, the person skilled in the art understands that the implant which results from this, may be found to be improved by the fact that it has turns which penetrate more deeply into the tissue, as if they were larger, since the material around the turns has been removed by the machine operation (thus reducing the residual width of the body) and that the pressure present in the surrounding tissues, in particular in the case of an implantation at an articular level, may assist the turn to sink into the bone more deeply. Further, the solidity of the implant may be found to be improved by the material preserved by the machining operation, whereas in the prior art only the thread is preserved and the turns (12) are alone for supporting the significant forces during and after screwing. Thus, a stable and solid implant may be obtained. In some of these embodiments, the second machining operation may for example be carried out tangentially to the perimeter of the body (10) resulting in windows (15) which may be flared from the inside to the outside of the body (10), as (further) illustrated for example in FIGS. 1A, 2A, 3B, 2C, 6C, 6D, etc. However, alternatively, the second machining operation may be carried out substantially radially (or along an oblique axis between the radial orientation and the tangential orientation) so as to obtain windows having at least one sharpened outer edge as detailed hereafter.

Figure 23A:
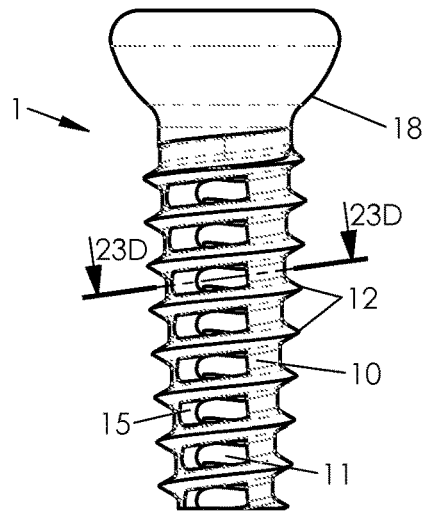
FIG. 23D illustrates a sectional view along the sectional plane 23D-23D of FIG. 23A, FIGS. 24A and 24B illustrate profile and sectional views respectively along the sectional plane 24B-24B of FIG. 24A, of an implant according to various embodiments.
Figure 23B:
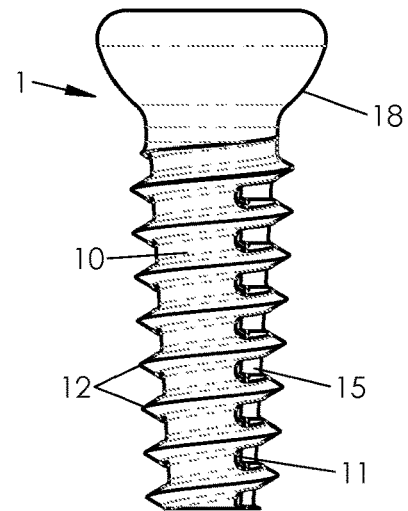
Figure 23C:
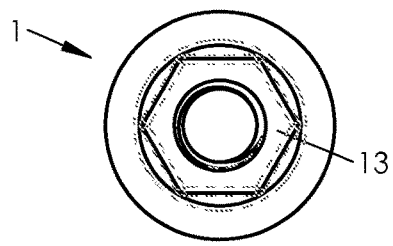
Figure 23D:
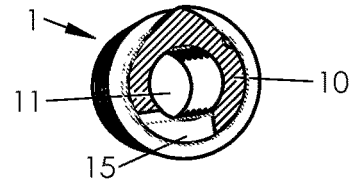
Figure 23E:
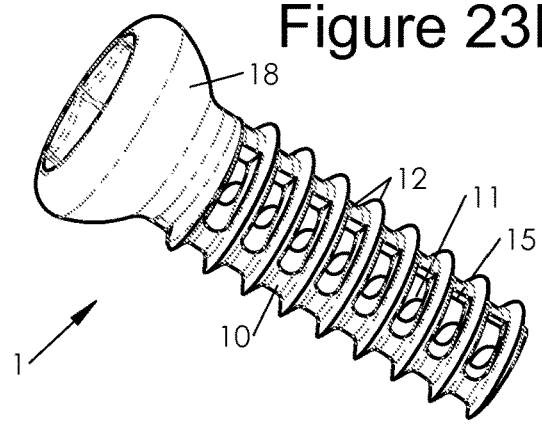

In certain non-exclusive embodiments, said windows (15) of the bone implant (1) advantageously may have at least one sharpened outer edge. Indeed, regardless of how the conduit and the windows are obtained, it may be useful to provide at least one sharpened outer edge for the windows (15). In particular, it may be generally preferred that the sharpened edge be the one which first attacks the bone during the screwing of the implant, so that this sharpened edge may gradually dig into the bone (for example by cutting out shavings) during the screwing. Thus, when the windows (15) are obtained by a second machining operation, the latter may for example be achieved along radial or oblique axis as explained above, so as to obtain one sharpened leading edge, as illustrated for example in FIGS. 23A and 23D (the right outer edge on the window of FIG. 23D has a cutting edge which allows cutting out of the bones or of the cartilage). Also, if the windows are obtained, as in the prior art, by longitudinal machining operations, it may be possible to provide the latter so as to make such a cutting edge, as illustrated for example in FIGS. 22C, 22D, 22E and 22F, which show illustrative and non-limiting examples of such machining operations (and moreover shows the fact that a variable number of machining operations may be provided for making the windows). This type of layout with at least one edge (preferably the leading edge) gives a possibility of at least sharpening or scraping out the bone during the screwing, which stimulates bone growth and stabilizes the implant, this also gives the possibility, optionally, of automatically filling (at least partly) the longitudinal internal conduit (11) during the screwing, which gives the possibility of limiting the resorting to exogenous bone tissue or to a substitute or to a cement, even if the latter may be used (additionally or alternatively) in various embodiments.

On the other hand, in certain non-exclusive embodiments, said head (18) of the implant (1) may be provided with stabilization means (2, 3, 5) (e.g. compression, locking, supporting means) of the implant, intended to bear upon the bone tissue around said head (18) (these stabilization means optionally comprising locking means for securing them on the implant). Various embodiments are described hereafter for the stabilization means but the person skilled in the art will understand from this functional definition that the implant may be provided so that its head (which may be generally the subsisting portion outside the bone tissue or the articular space) may be stabilized on the bone tissue (on a bone surface or on the edges of the joints).

Various embodiments described in the present application generally relate to a bone implant (1) which may be in particular useful for implantation at articular facets of two adjacent vertebrae, i.e. between two facets (intra-facet implant) or through both facets (trans-facet implants). The threading (12) may be therefore particularly adapted to screwing in bone or articular tissue. In certain embodiments (not shown), particularly useful in the case of an implantation of the body (10) in the inter-facet space, the implant may include a second body, also with an elongated shape along a longitudinal axis and substantially parallel to the first body (10). This second body (generally cylindrical or conical or frusto-conical like the first body) may be preferably provided with a thread adapted to screwing in bone tissue. Screwing in the cartilage may be thus obtained by the first body and screwing in one of the facets (and no longer at an articular level) or in one of the pedicles may be obtained by means of the second body. This type of solution allows proper stabilization of the implant. The second body may be generally positioned at a distance from the first body which may be provided for avoiding cracking or fracturing of the bone tissue by the screwing of both bodies. The second body may be thus maintained at a distance from the first body, preferably with stabilization means such as those described in the present application. In particular, in various embodiments, the present application describes stabilization means comprising rods or a bell and the person skilled in the art will note that these stabilization means may be mounted on the implant through portions which generally have thickness provided for giving good solidity, unlike certain implants of the prior art provided with thin plates which risk becoming twisted or breaking. Also, the head or the portion of the implant which is intended to remain outside the bone tissue may be generally provided so as to have a restrictive height, so as to avoid a too large protrusion (or projection) which has the risk of damaging surrounding tissues or of loosening the implant by the contact with other structures. Thus, both of these types of layout may be sometimes combined in certain embodiments so that a head with a small height may be provided with stabilization means, notably those provided with a second body maintained at a distance from the first body (10), the thickness of which represents at least one third of the height of the protruding portion of the implants at the surface of the bone tissue. This type of combination gives the possibility of providing a particularly stable implant since it has a head which may be little subject to aggressions (outer aggressions) and solidly retained by stabilization means which further protect this head from such aggressions. On the other hand it will be noted that in the case of a second body maintained at a distance from the first body (10), a body provided with a head of restricted dimensions, for example with a height not exceeding the thickness of the portion connecting both bodies together may be preferably selected but it is generally preferred that the second body have a length which is not less than 1 quarter of that of the first body, in order to provide efficient stabilization. Finally, it will be noted that such a second body may share with the first body or all part of the other technical features described in the present application.

Various independent but not exclusive embodiments detailed above represent solutions further having the advantage of being able to be used either as a trans-facet implant, or as an inter-facet implant, for example by the fact that the implants provides a wide space for bone grafting in its internal conduit and/or that the bone may be sharpened by the passage of the implant and/or that the stability of the implant may be improved relatively to the known solutions.

Figure 13A:
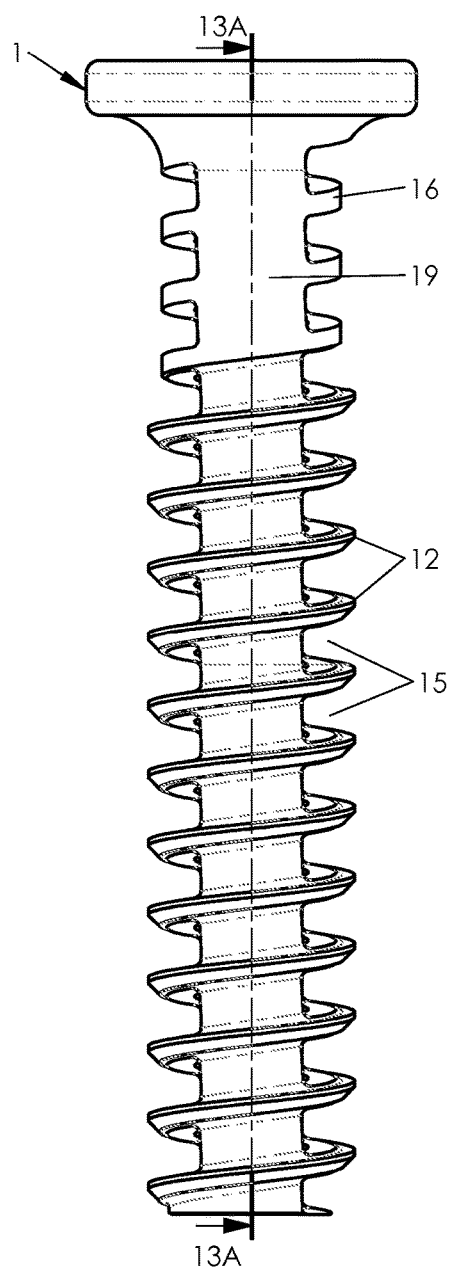
Figure 13B:
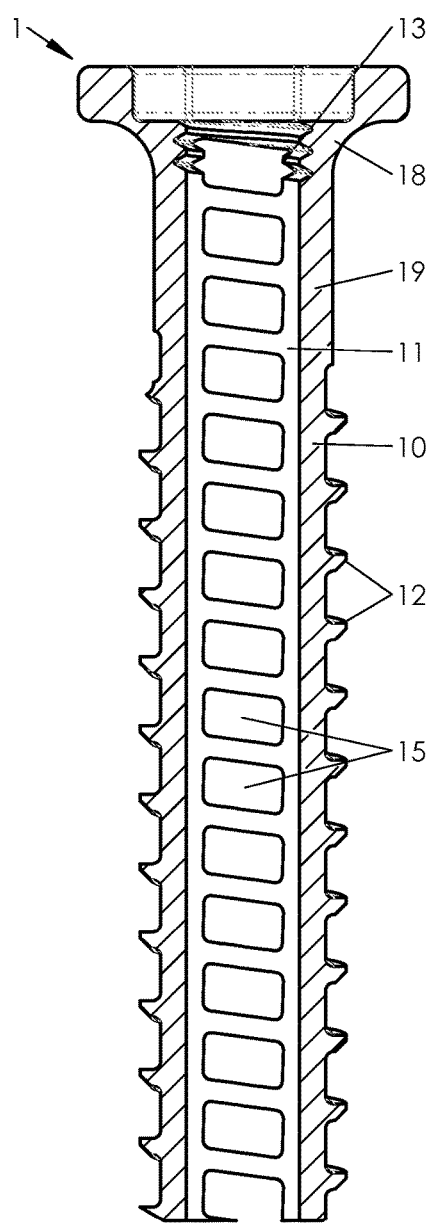
Figure 19A:
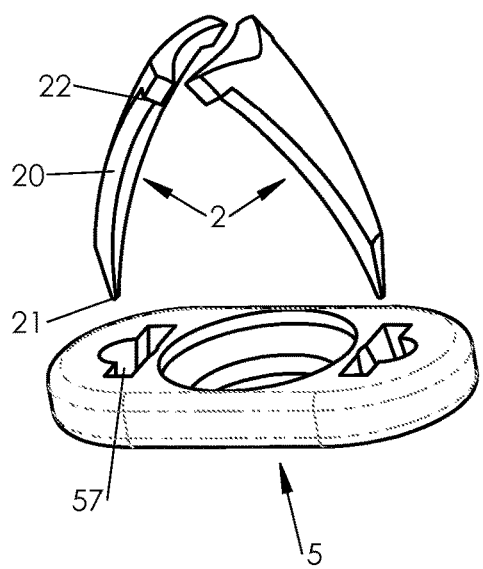
FIG. 19C illustrates a perspective view of an implant provided with such stabilization means.
Figure 19B:
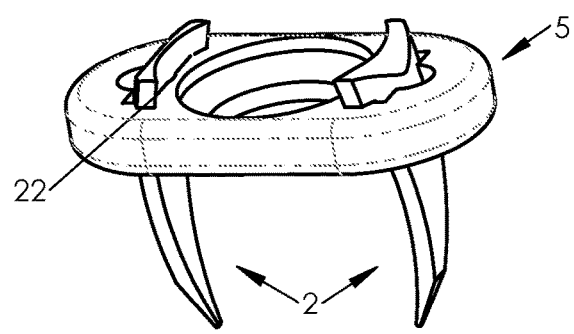
Figure 19C:
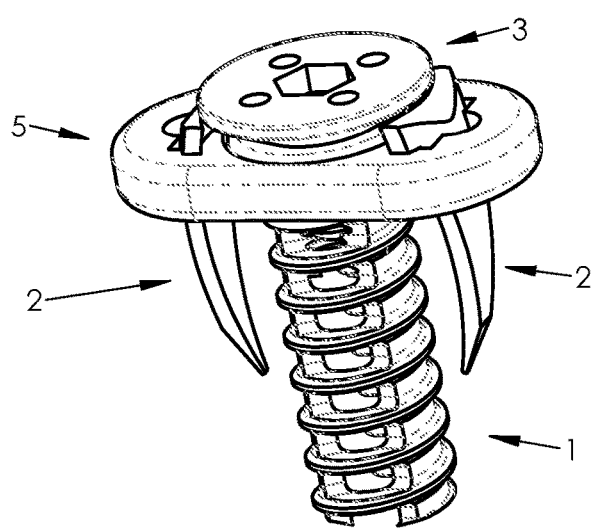
Figure 25A:
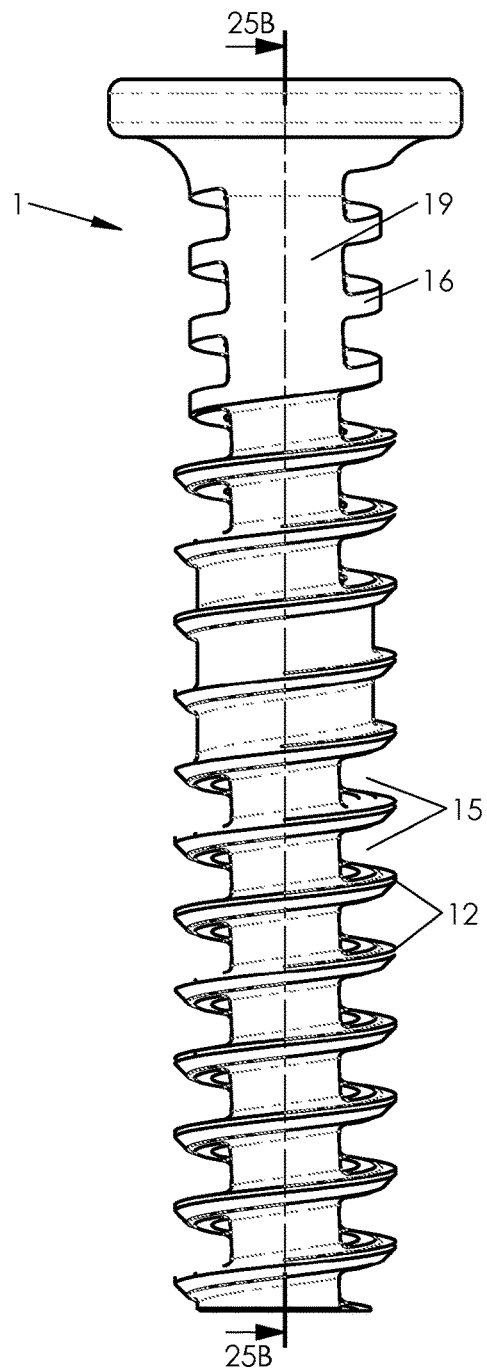
FIGS. 25A and 25B illustrate profile and sectional views, respectively, along the sectional plane 25B-25B of FIG. 25A, of an implant according to various embodiments.
Figure 25B:
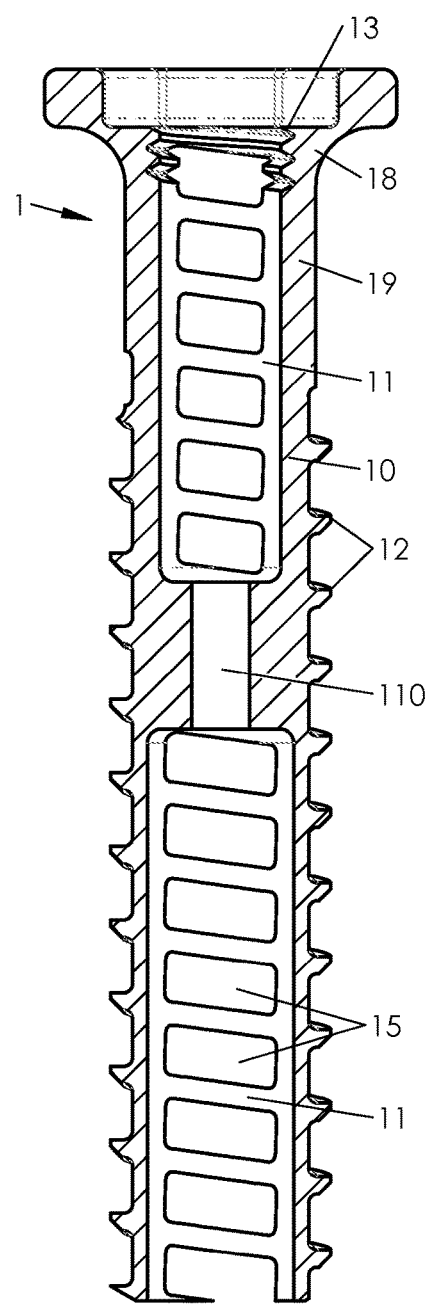

Further, it may be sometimes preferable, for better solidity, to keep a solid body at the portion on which the largest forces will be exerted, such as for example the portion which may be finally positioned between the facets and/or the one where the forces transmitted through the stabilization means are exerted. Thus, said "at least one portion of the longitudinal axis" in which is made the internal conduit (11) may sometimes be a distal portion (on the side of the end opposite to the head) or median portion, notably in the case of an intra-facet implantation, but may also be more proximal. Nevertheless, the body may be hollow and solid on variable portions along the longitudinal axis, for example according to the intended uses for the implant. Further, it may be generally preferred that the body (10) be hollow over the whole of its length, so that the implant may be more easily implanted by means of a pre-positioned broach like in the known techniques of the prior art and allowing that the implant, slipped onto the broach, may slide as far as its implantation site and may then be screwed into the bone tissue (or cartilage tissue, moreover it will be noted that the terms of "bone" or "osseous" designate in the present application both the bone and the cartilage). It may be therefore preferable to provide at least one passage for such a broach, even if at least one portion not including any longitudinal internal conduit is used. Thus, for example, FIGS. 24A and 24B illustrate in an illustrative and non-limiting way an implant comprising a hollow proximal portion, a solid median portion and a hollow distal portion, while FIGS. 25A and 25B illustrate an implant of the same type, but in which the median side portion however may include a passage (110) for such a broach and/or for communication between the two grafting chambers provided by the two longitudinal internal conduits. The person skilled in the art will understand that various alternatives for positioning and dimensioning various conduits and passages are possible. Indeed, the rigidity of the implant or of certain portions may vary depending on the internal conduit or passage which may be, along the longitudinal axis, big, and then small, and then big, etc., as illustrated for example in FIG. 16B where the two internal conduits (11) communicate through a larger passage than the one illustrated in FIG. 25B. Further, it will be noted that it may be possible to make windows (15) at the portions having such a passage, as for example in FIG. 16B, or to prefer not making them as in FIG. 25B. This remains true regardless of the size of the passage and regardless of the method for making the windows (longitudinal or transverse machining operation), insofar that the diameter of the latter does not exceed a certain value beyond which it may necessarily open onto the outside of the body. Further, instead of providing a longitudinal internal conduit (11) providing a substantially cylindrical grafting chamber, as illustrated for example in FIGS. 13A and 13B, it may be possible to provide conduits and/or passages (broach and/or communication passages in particular) with a conical shape, as for example illustrated in FIGS. 14B and 15B. Such a shape has the advantage of providing a grafting chamber size and a solidity of the implant which may be variable along the longitudinal axis. Depending on the needs, it may therefore be possible to adjust the conduits and/or passages for obtaining more or less solid portions and/or intended to provide more or less wide grafting chambers. It will be noted that any combinations of conduits and/or passages with a conical or frusto-conical shape with solid portions or provided with a more or less wide passage, are possible and within the scope of the present description.

In certain embodiments, said free end of the body (10) is self-drilling. By the term of "self-drilling" is meant here that this end is capable of drilling the bone tissue by itself. Such a functional definition may simplify the application with a pointed shape of the end but may also be advantageously obtained with a split head or by the fact that a window (15) may be present on an extreme distal portion and provides a cutting surface giving the possibility of drilling into the bone tissue. FIGS. 26B and 26C illustrate an example of a pointed free end. In this example, the end may be solid and it may be provided with a notch (112) which provides a cutting edge allowing easy penetration into the bone. It will be noted that it may be possible to provide that this free end is not solid, but rather hollow, as illustrated for example in FIG. 27C where it includes a passage (111) (narrower than the internal conduit) or for example, because the internal conduit (11) extends as far as this distal end. On the other hand, instead of a notch on a pointed end, it may be possible to provide a notch on a cylindrical or conical or frusto-conical end, but it may be also possible to provide that the drilling function be obtained through at least one window (15) at the distal end. Thus, for example, a window (15) may be made, which extends over several turns (12) and which provides a cutting edge with which the bone may be sharpened more easily.

Moreover, it will be noted that in many embodiments illustrated in the figures, the windows (15) may be made between the turns (12) of the threading and generally between the totality (and the quasi-totality) of the turns. However, it may be possible to make these windows only on one portion of the turns. Thus, at least one portion of said windows (15) may be for example separated by at least two turns (12) without any window (15). Conversely (but not exclusively and in a way which may be combined with various embodiments detailed above), like for the free end, it may be possible to provide on various portions (proximal, median or distal portions), windows which extend over several turns rather than being confined to the space between two turns. Thus, in certain embodiments, at least one portion of said windows (15) is made on several turns (12).

Thus, it is understood from the foregoing that various combinations of the features discussed in the present applications may be contemplated, such as for example a conical implant body with cylindrical threads which may be provided so as to enhance the bone engagement at the end and facilitate the self-filling effect, and optionally with windows of variable dimensions, for example, mainly greater at the end for also promoting the self-drilling or self-tapping aspect in this case.

As regards the turns (12) of the threading of the body, it is understood that they may be provided on all or part of the body, whether this is along the longitudinal axis or around the latter. For example, portions (19) may be provided, wherein no turn/thread exceeds the perimeter of the body, even if windows may be all the same made on these portions, such as for example as illustrated in FIGS. 9A, 9B, 9C, 13A, 13B, 14A, 14B, 15A, 15B, 16A, 16B. Further, it will be noted that these illustrative examples of the figures show such portions (19) at a generally proximal level since it is there where it may be less necessary to have turns deeply anchored in the bone tissue, but various alternatives are of course possible. On the other hand, in certain embodiments, the turns (12) of the threading may be "retentive", i.e. they have a shape which promotes retention of the implant in the bone tissue. Such a function may be fulfilled by the fact that the turns have a face (120) facing the proximal head (the head) which may be opposed to the withdrawal of the implant, for example by the fact that this face may be oriented in a plane substantially perpendicular to the longitudinal axis, or even slightly tilted toward this proximal end, as illustrated for example in FIGS. 27C and especially 28B.

Further, in order to facilitate implantation, the other face (121) of the turns (the one facing the distal end) may be tilted in order to facilitate penetration, i.e. it may be preferably not parallel to the longitudinal axis but rather tilted towards the distal end, as illustrated for example in FIG. 28B. Nevertheless, this useful layout is not limiting and the geometry of the thread may be diverse such as for example trapezoidal, triangular, etc.

As regards the pitch of the threading, i.e. the spacing of the turns along the longitudinal axis, the present application also provides various types of non-limiting layouts which may be useful depending on the conditions. In particular, in certain embodiments, the turns (12) of the thread (or by extension the thread (12) of the implant) have variable pitch which shortens in the direction of the head (18). Also, in certain embodiment, the body (10) may be provided with several threads (12) with different pitches. Preferably, the pitch of a thread located on the side of the free end may be of a larger size than the adjacent thread located on the side of the head (18), so that the pitch of the thread may be gradually reduced upon advancing towards the head. This type of layouts with variable pitch gives the possibility of obtaining a compressional effect. Indeed, when such an implant with variable pitch or comprising several threads with decreasing pitches may be screwed in, a compressional effect may be obtained which is for example particularly useful in the case of screwing in a bone structure where it may be desired to properly flatten the structures together, like for example a trans-facet implantation.

In a general way, the implant may be inserted so that the majority of the body (10) penetrates into bone or cartilage tissue or between two bone structures and so that the head remains on the outside, but it is possible to provide that the head is at least partly intended to be also inserted inside the treated structures. Preferably, it may be provided that the head remains on the outside and various embodiments of the present application provide in a useful way that the head bears upon (and is therefore on the outside) the surfaces. As various embodiments provide at least one internal conduit (11), it may be useful to block the latter so as to avoid bone growth risks at the surface of the treated portions and/or invasion risks of the interior of the implant by other tissues or undesirable organisms. Thus, in certain embodiment, the said head (18) of the implant (1) closes the longitudinal internal conduit (11) or may include means (3) for closing the longitudinal internal conduit (11). Such closing means give the possibility of providing an implant capable of being slipped onto a broach assisting the implantation like in the prior art and nevertheless allows the implant to be blocked after implantation. However it will be noted that various embodiments in fact may include means for stabilizing the implant, as detailed hereafter, which generally may include locking means which may, according to various embodiments, fulfill this function for closing the implant. Nevertheless, in various embodiments, the locking means may be laid out so as not to block the implant so that the locking of the stabilization means may be achieved in the presence of an optional broach; it may then be possible to either provide or not closing means for blocking, according to various embodiments. Such closing or blocking means may for example include at least one screw or a bolt mating a tapped hole in the head, but may also include a plug provided with lugs intended to be fastened with clips in an accommodation of the head, or any other means within the reach of the person skilled in the art.

Figure 3A:
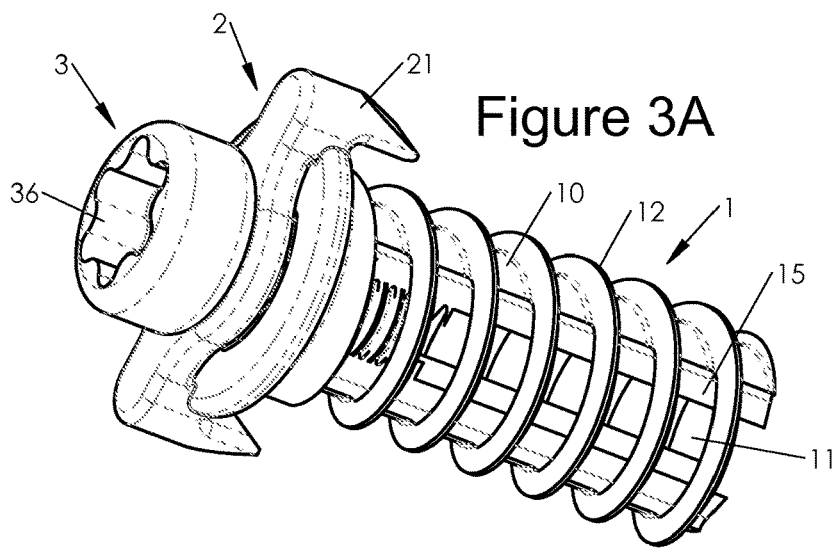
FIG. 3A illustrates a perspective view of an implant provided with stabilizing and locking means according to various embodiments.
Figure 3B:
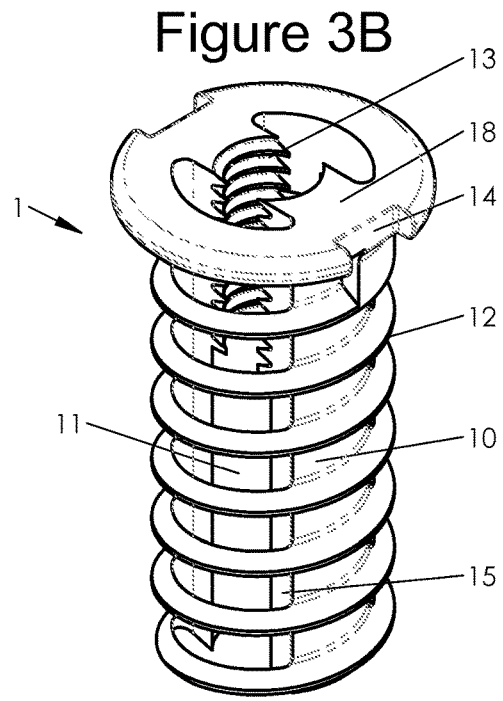
FIGS. 3B, 3C and 3F illustrate perspective, profile and top views, respectively of an implant body according to various embodiments
Figure 3C:
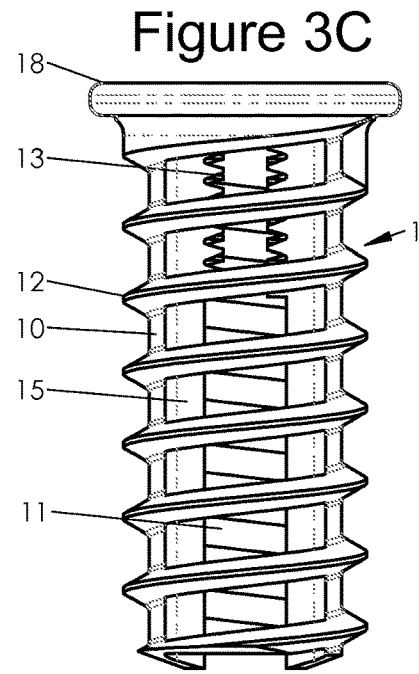
Figure 3D:
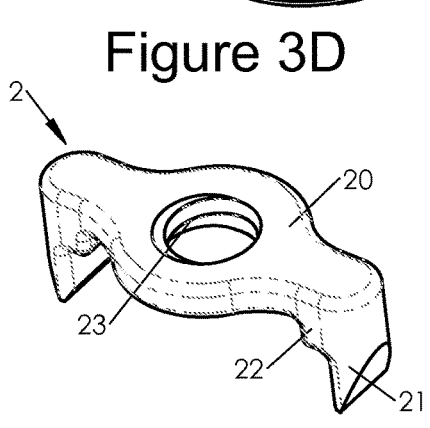
FIGS. 3D and 3E illustrate perspective views of a stabilization element and of a locking means, respectively, according to various embodiments.
Figure 3E:
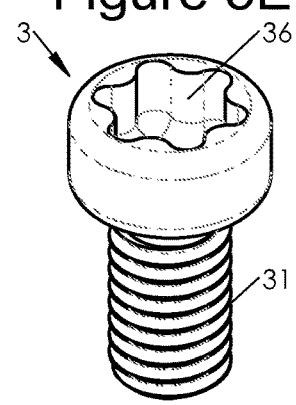
Figure 3F:
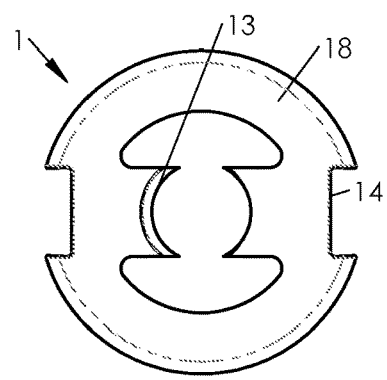
Figures 4A, 4B:
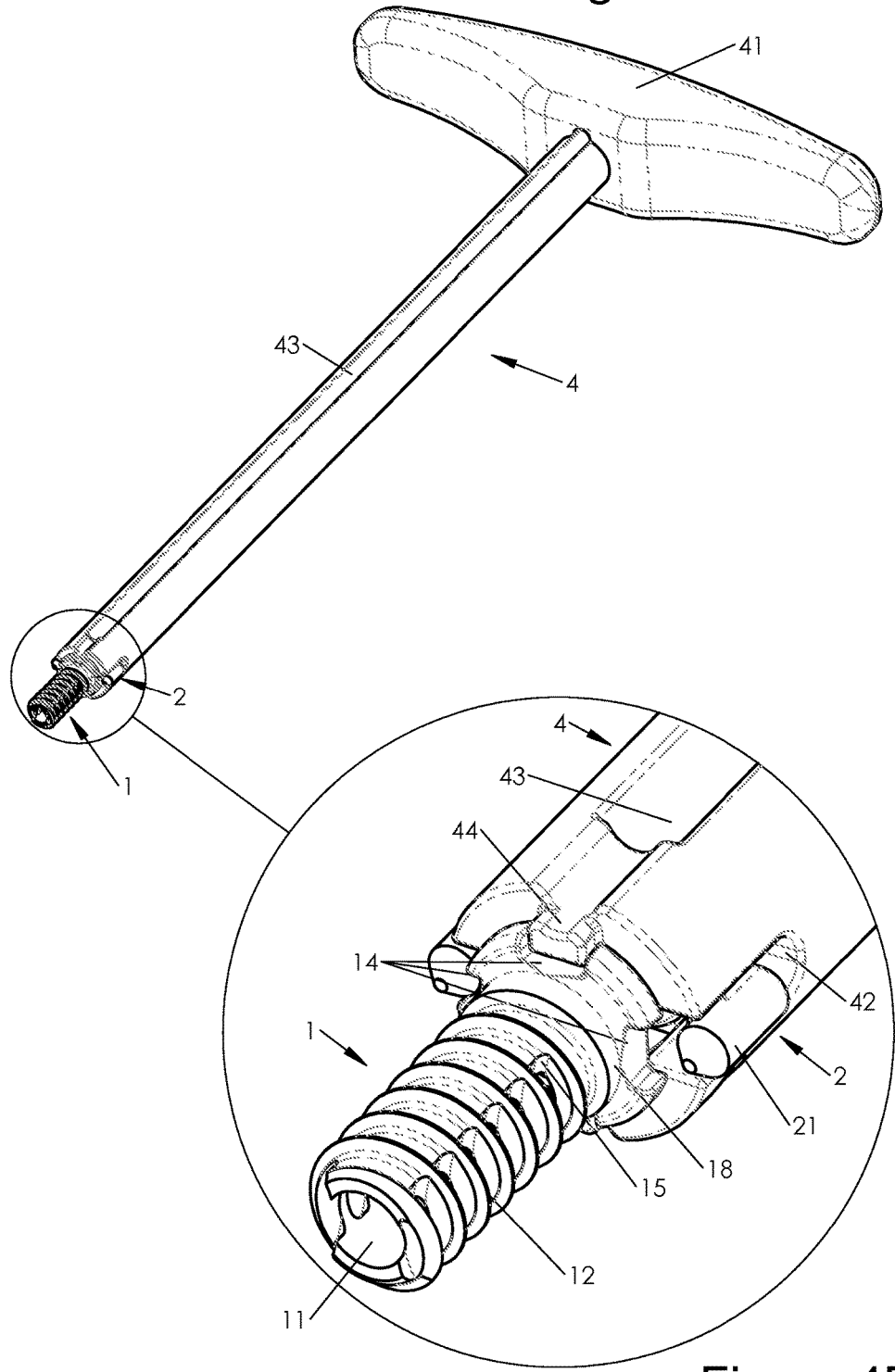
FIG. 4A represents a perspective view of an implant-holder retaining an implant according to various embodiments and FIG. 4B illustrates an enlargement of this implant-holder at its portion retaining the implant.
Figure 7A:
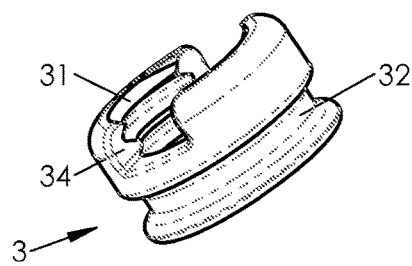
Figure 7B:
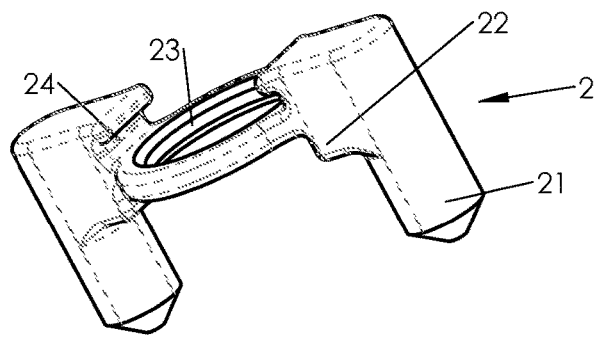
Figure 7C:
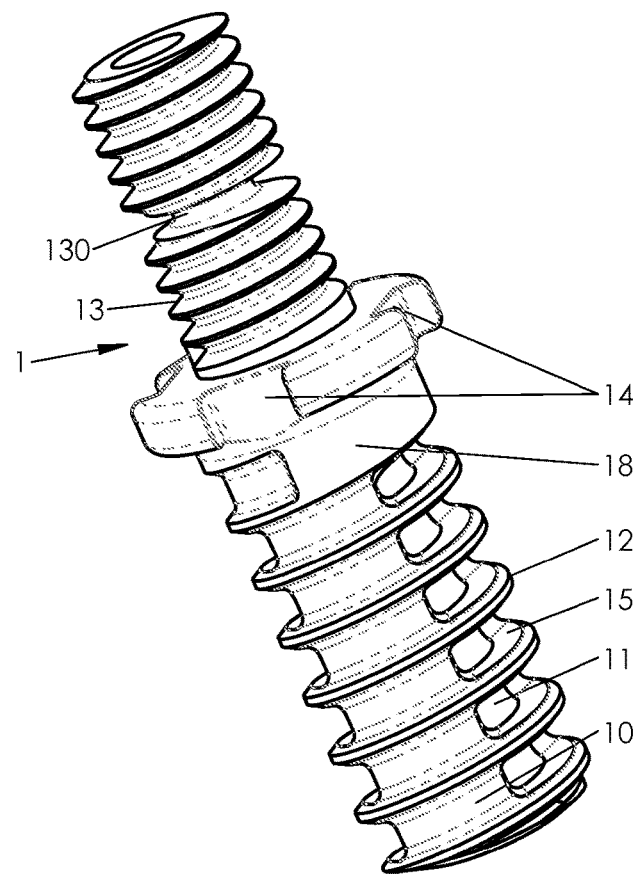

In certain embodiments, said head (18) of the implant (1) is provided with means (2, 3, and 5) for stabilizing the implant, which may be preferably intended to bear upon the bone tissue around said head (18). In certain of these embodiments, said stabilization means (2, 3, 5) may include at least one stabilization element (2) forming a kind of staple comprising at least two rods (21) substantially parallel to the longitudinal axis and able to penetrate the tissue around the head (18) and possibly a portion of said body (10) in proximity to said head (18). Examples of such stabilization means (2) are for example illustrated in FIGS. 2C, 3D, 7B showing elements comprising a ring intended to be slipped onto a portion of the head and at least one tip intended to be planted into surrounding tissues. In certain of these embodiments, said rods (21) of the stabilization element (2) have a pointed free end. The term of "pointed" in said description in fact more widely designates the fact that a structure may be able to penetrate the bone tissue, by therefore covering beveled structures as well as pointed structures in a non-limiting way. Further, in certain embodiments, said rods (21) may be connected together through a ring (23) making the stabilization element (2) able to be mounted on said head (18), as illustrated for example in FIGS. 2C, 3D, 7B, but the person skilled in the art will appreciate that this type of mounting on the head is only an illustrative and non-limiting example since various layouts may give the possibility of mounting means for the stabilization means on the head (or on any other portion of the implants optionally). According to various alternatives, the ring (23) may be slipped or screwed onto a high portion (13) which juts out from the head (18), as illustrated for example in FIGS. 6A, 6B, 6C and 6D, whereas, in other alternatives, the ring rests on the head and its aperture may be able to receive a low portion (13) of locking means (3) which may be attached in the head of the implants as illustrated for example in FIG. 1D or 3A. It will be noted that the figures show threadings and tappings for attaching locking means on the head but that various types of layouts are possible as detailed above with reference to the means for closing the implant.

In certain embodiments, in particular those comprising a stabilization element (2) provided with two rods (21) intended to penetrate the bone tissue around said head (18), the latter may include at least two notches (14) able to receive said rods (21) or shoulders (22) positioned along said rods (21) as illustrated for example in FIGS. 1A, 1B, 1C, 1D, 2A, 2C, 2D, 3A, 3B, 3D, 3F or 6A, 6B, 6C, 6D, 7B and 7C. Such notches (14) give the possibility of imposing the positions of the rods (21) around the implant, so that it may be possible to provide that they be ideally positioned relatively to the treated bone structures (notably so that they are each planted in one of the adjacent vertebrae during an intra-facet implantation). Further, the presence of a shoulder (22) (and of material between the center of the stabilization element and said rods) allows said rods to be maintained at a distance from the body (10), so that these rods may be planted at a distance promoting better stabilization than if they had been closer to the body of the implant.

Figures 5A, 5B, 5C, 5D:
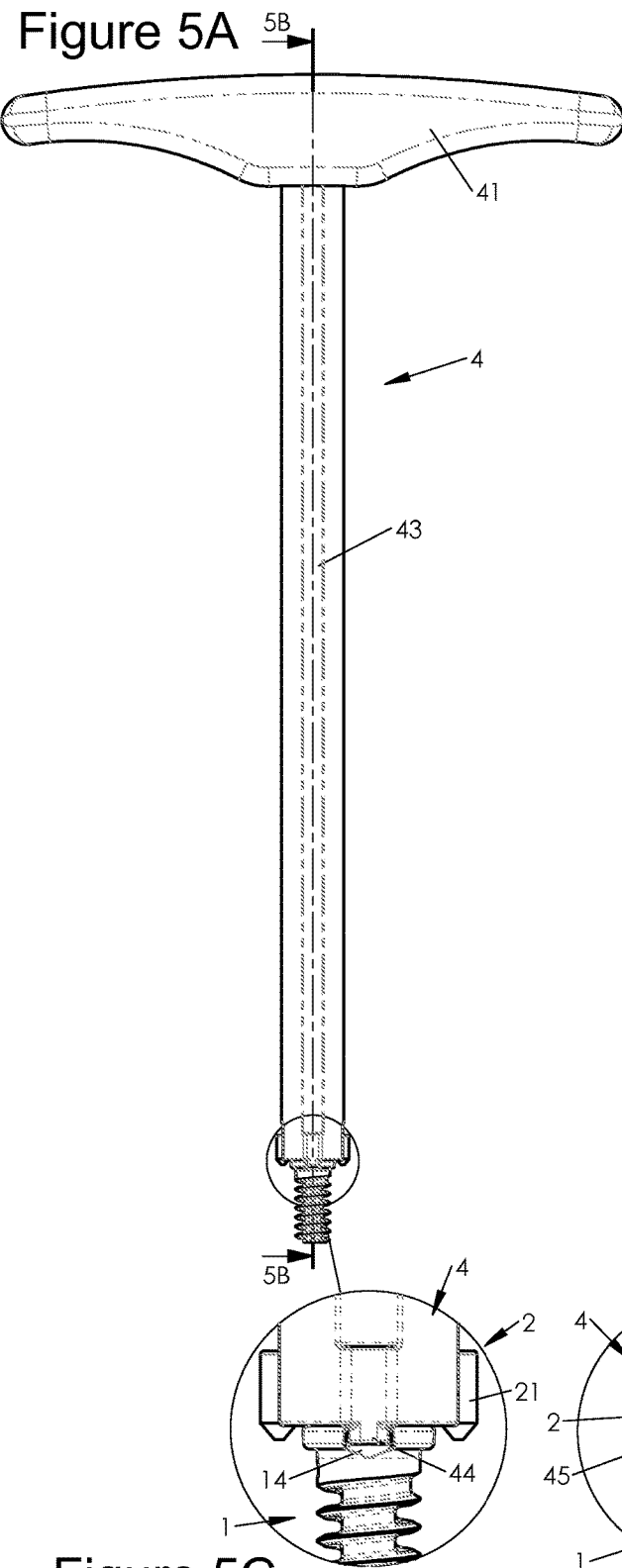
FIGS. 5A and 5B illustrate profile and sectional views respectively along the sectional plane 5B-5B of FIG. 5A, of an implant-holder retaining an implant according to various embodiments
FIGS. 5C and 5D illustrate enlargements of the figures, notably of FIGS. 5A and 5B.
Figure 6A:
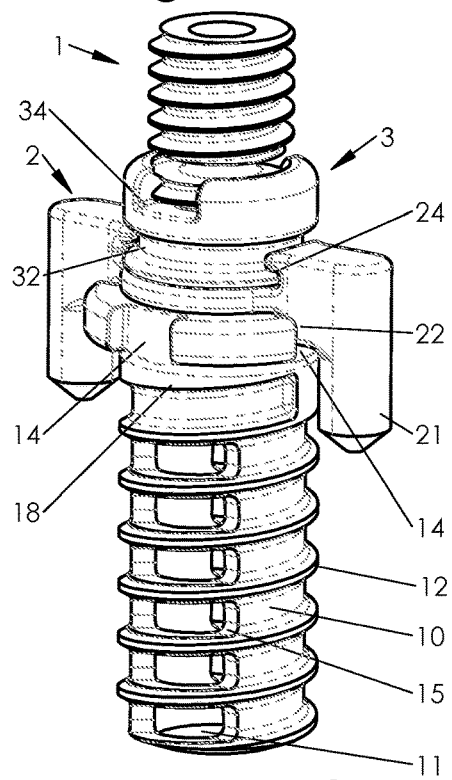
FIGS. 6A, 6B and 6C illustrate perspective, face and profile views respectively of an implant according to various embodiments.
Figure 6B:
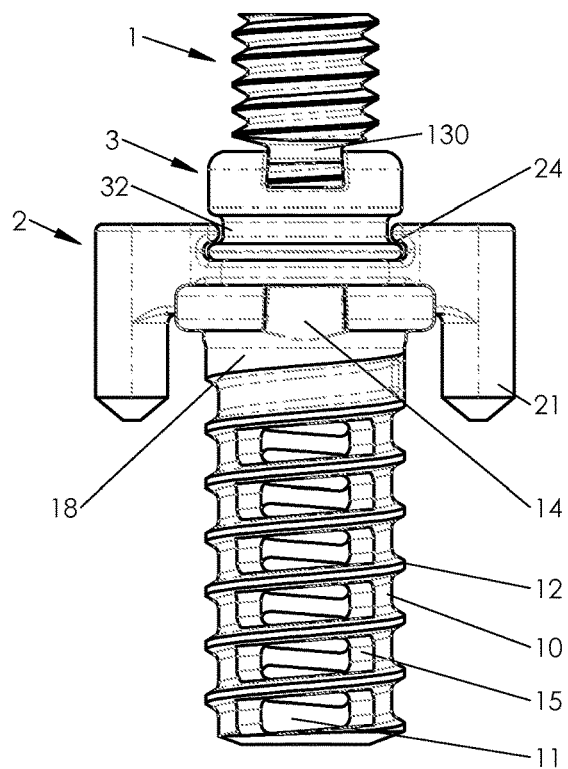
Figure 6C:
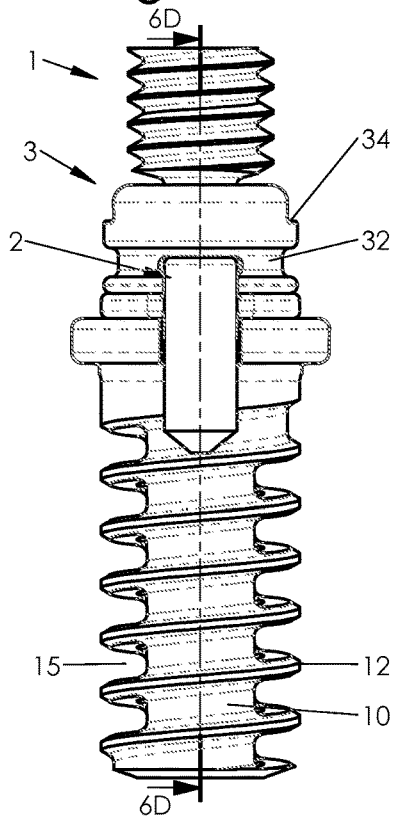
Figure 6D:
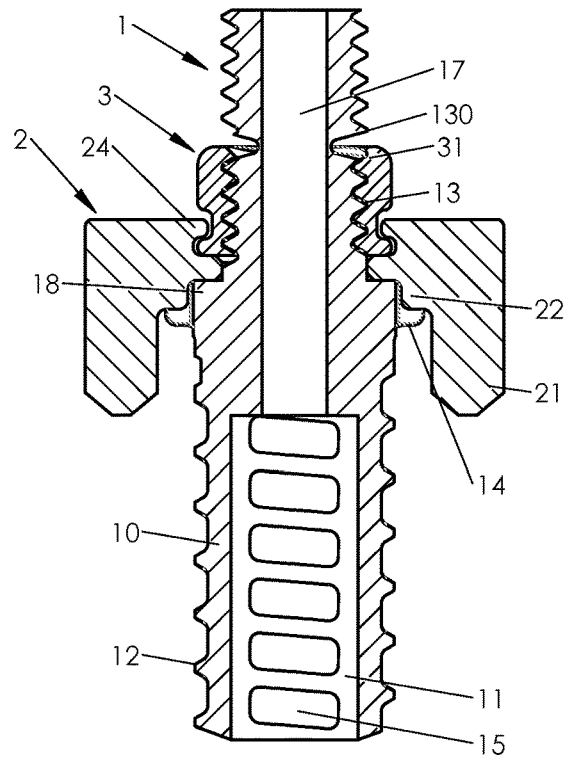
FIG. 6D illustrates a sectional view along the sectional plane 6D-6D of FIG. 6C, FIGS. 7A, 7B and 7C illustrate perspective views of a locking means, of a stabilization element and of an implant, respectively according to various embodiments.
Figure 8A:
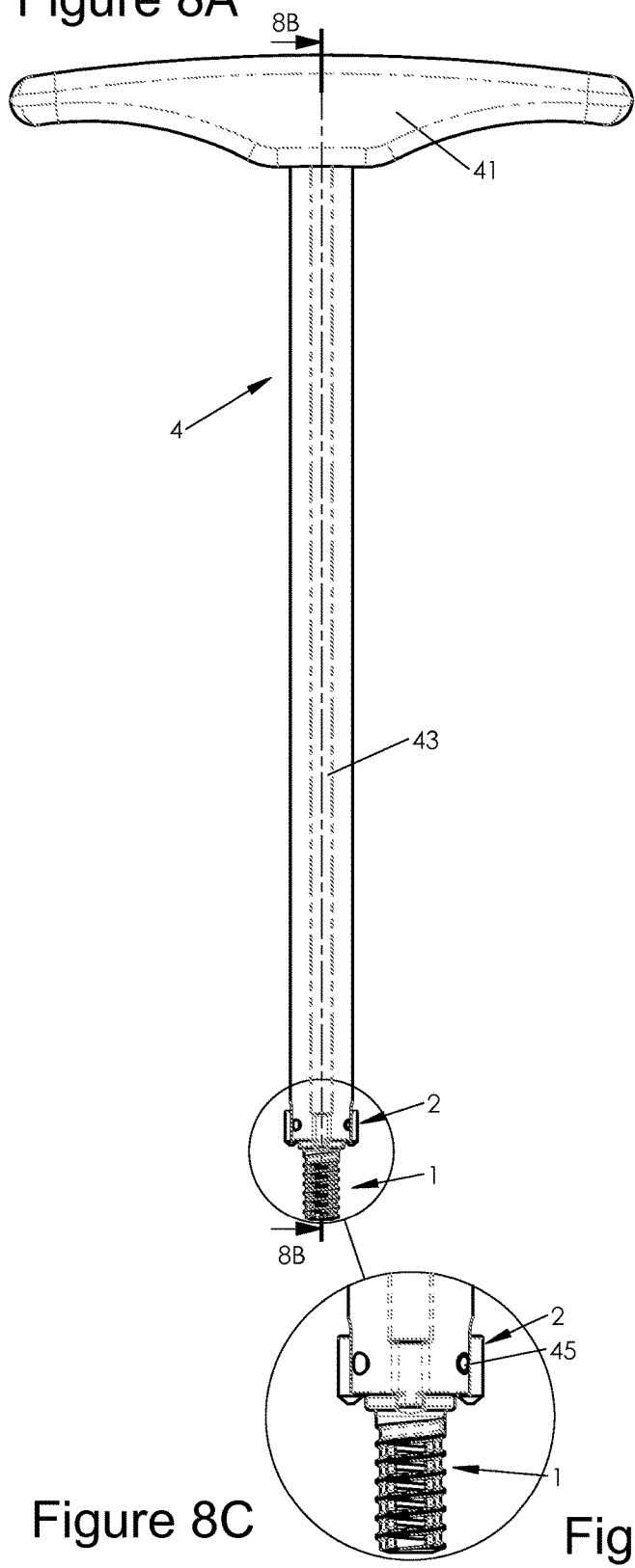
FIGS. 8A and 8B illustrate profile and sectional views respectively along the sectional plane 8B-8B of FIG. 8A, of an implant holder retaining an implant according to various embodiments
Figure 8B:
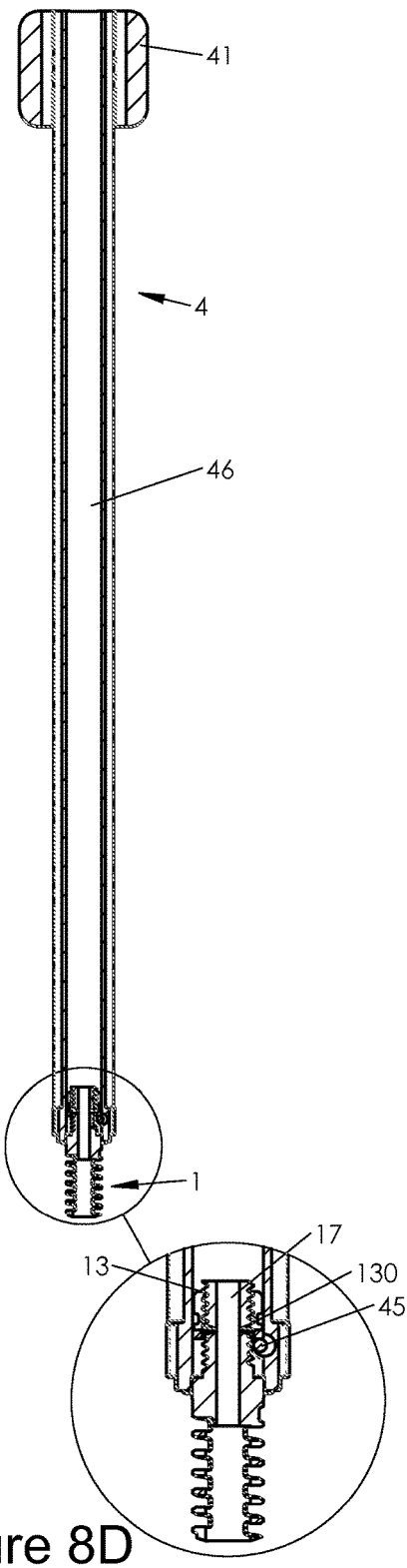
Figure 8C:
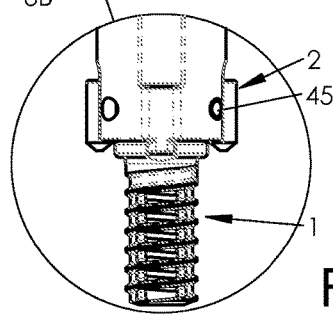
FIGS. 8C and 8D illustrate enlargements of the figures, FIGS. 8A and 8B respectively.
Figure 8D:
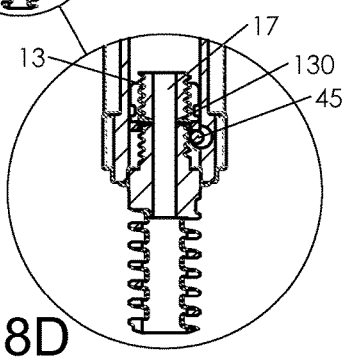
Figure 10A:
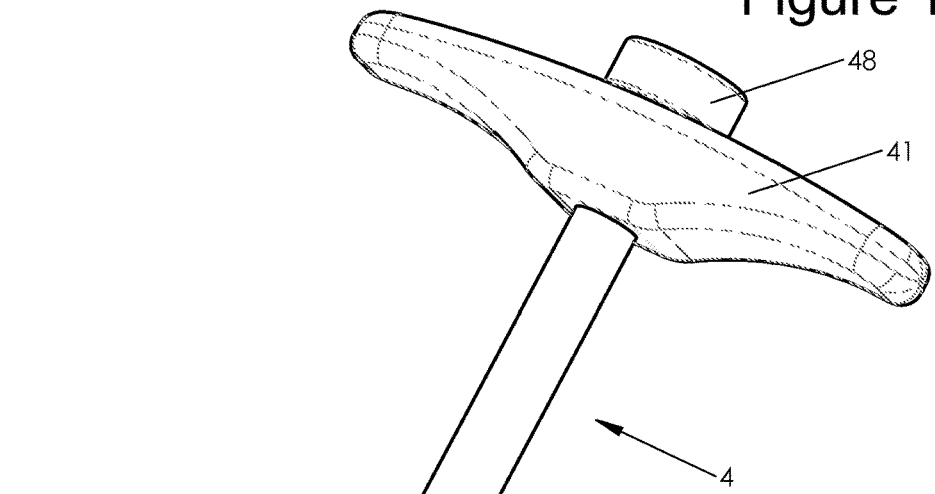
FIG. 10A illustrates a perspective view of an implant-holder retaining an implant according to various embodiments and FIG. 10B illustrates an enlargement of this implant-holder at its portion retaining the implant.
Figure 10B:
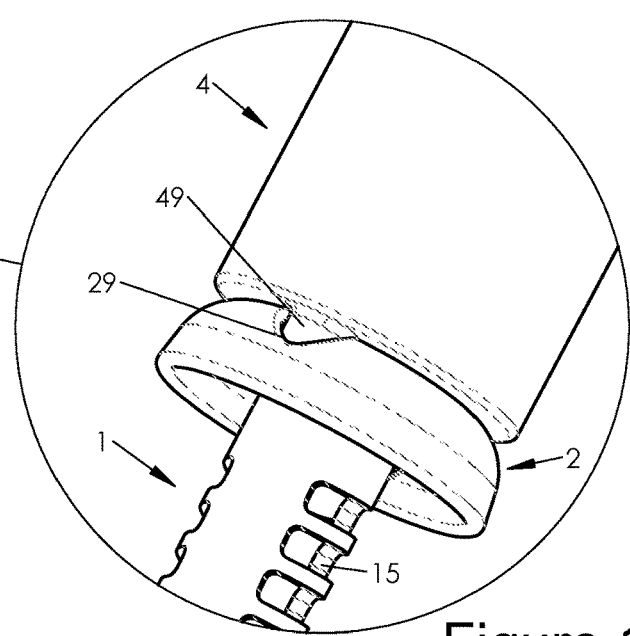

Further, in certain embodiments, an instrument (4) is provided for the implantation of various embodiments of the implant (1). Such an instrument (4) generally may include an elongated body between an end which may be handled by means of a handle (41) for example and an end holding the implant and preferably may include an internal conduit (46), as illustrated for example in FIGS. 5B and 8B, so as to be able to be slipped on around a guiding broach as detailed above. Further, in order to facilitate implantation, such an instrument (4) may include at its end intended to hold the implant at least one lug or protrusion (44) mating at least one notch (14) of the instrument as detailed above. The cooperation between this lug (44) and the notch (14) allows actuation of the implant in rotation by the instrument so as to screw the implant into the structures to be treated. Further, the instrument (4) sometimes may include on the perimeter of its tubular body at least one groove (43) able to receive a piercing tool allowing the bone tissue to be pierced, into which the rods (21) of the stabilization element may be inserted. In such embodiments, the implant preferably includes a number of notches (14), double the number of rods (21) present on the stabilization means, in order to facilitate the implantation as detailed hereafter. In such embodiments, the implants for example may include 4 notches regularly positioned around the longitudinal axis of the implant and so that the instrument allows the implant to be gripped with its diametrically opposite lugs (44), while the rods (21) of the stabilization element (2) may be held by the instrument and engaged into the other notches, for example in a radial position shifted by 90° relatively to the lugs (44). Thus, it may be possible by moving the instruments backward, to perform a rotation by a quarter of a turn in order to bring the rods so that they face the notches (14) via which a perforation was made in the bone tissue and to thus introduce these rods into the holes. This type of layout facilitates the implantation by allowing preliminary piercing and by avoiding that the rods (21) interfere with the screwing of the body, for example as in the case when they would be provided to be interdependent with the body (10) in rotation. It will be noted that the term of "rod" is used here for designating the structures intended to penetrate into the bone tissue around the body, but it is clear that the shape of such stabilization means may vary and provision may be made for using plates, with a variable section and optionally T, V, H or U sections in order to provide better strengths in several dimensions. In the case of plates, it will be noted that they may be pointed or sharpened, optionally to the point of not requiring any preliminary perforation. The instrument preferably includes means for retaining the implants and generally a retaining element (45) for the locking means, as illustrated for example in FIGS. 5D and 8D. In these examples, the implants may include a tapped hole (31) able to receive threaded rods (13) of the locking means (3) as illustrated for example in FIGS. 1D, 2D, 3B, 3C, 3F, or may include a threaded rod (13) able to receive a tapped hole (31) of the locking means (3) as illustrated for example in FIGS. 6D, 7C, 8D. Such a retaining means (45) may then for example include a rod intended to be flattened against the threaded rod (13) and thereby retain the assembly as illustrated in these examples of figures or may include a threaded rod (46) (preferably tubular for the guiding broach) cooperating with a tapped hole (31) of the implant, as illustrated for example in FIG. 18C. Further, the instrument may include, at its end retaining the implant, means for transmitting the rotation, such as for example planar surfaces not tangent to the perimeter of the implant and cooperating with substantially identical orientation surfaces of the implant, such as for example a nut-shaped end intended to penetrate into a six-sided accommodation of the implant, as shown in the illustrative example of FIG. 17B for example. In the examples of FIGS. 6A, 6B, 6C, 6D, 7A, 7B, 7C, 8A and 8B, it will be noted that the implant in fact may include a threaded rod (13) jutting out from the head (18) and provided with a self-breakable portion, for example obtained by means of a notch (130) as for example visible in FIG. 7C. The person skilled in the art will understand from the various technical considerations above that various layouts are possible for retaining the implant and that the means and elements above are illustrative and non-limiting.

In certain embodiments, said stabilization means may include at least one bell-shaped stabilization element (2) mounted on (or secured to) the head (18) and the perimeter (21) of which may be intended to bear upon the bone tissue surrounding the head (18) as illustrated for example in FIGS. 9A, 9B, 9C, 10A, 10B, 11A, 11B, etc. In various embodiments, the bell secured to the head may be formed in a single piece with the head or may be attached above. In other embodiments, the bell may be movably mounted around the head. Further, the bell may be of the same material as the body of the implant (generally a solid metal material, such as for example titanium), but it is possible to provide a bell in another notably more flexible material, so that it may be crushed during the final screwing of the locking means and thus promotes efficient compression. A possible and useful material for this type of alternative embodiments is PEEK well-known in the field.

In certain embodiments, the bell is movable and allows a support of "polyaxial" type, i.e. it may be locked in diverse positions relatively to the longitudinal axis of the implant. For example, in certain of these embodiments, said head (18) has a peripheral lower surface (180) with the shape of a sphere portion, as illustrated for example in FIGS. 18C, 22A, 22B, 22E, 22F, 23A, 23B, 23E, 28A and 28B. Such a surface may be generally provided so as to be complementary to an internal upper surface of said bell (2) thus jointed on the head (18) of the implant, as illustrated for example in FIG. 12C, so as to allow an adjustment of the orientation of the bell relatively to the axis of the head. Further, it will be noted that in such embodiments, it may be preferred to use a limited sphere portion instead of a complete sphere or with too large dimensions, so that the portion of the implant which subsists at the surface of the bone tissue is not too exposed to aggressions (notably outer aggressions), as already detailed in the present application. Indeed, even if the range of possible orientations of the bell may be thereby restricted, it remains generally sufficient and the implant may be clearly more stable than with a large angle and especially a larger protrusion at the surface of the bone tissue.

In certain embodiments, said bell (2) may include at least one tip or tooth on its perimeter (21) for facilitating bone anchoring as illustrated for example in FIGS. 12A, 12B and 12C. This type of layout of the low portion of the bell, intended to bear upon the bone tissue, gives the possibility of improving the adhesion of the bell on the latter and thus improves the stability of the implant.

In certain embodiments, said stabilization means may include at least one plate (5) mounted around the head (18) and provided with at least one passage (57) able to receive a stabilization element (2), a so-called anchor, in the form of a plate (20) able to be anchored in the bone tissue around the head (18), as illustrated for example in FIGS. 19A, 19B, 19C, 20A, 20B and 20C. Like for the rods (21) described in the present application, the plates (20) may have diverse shapes and this term is not limiting, although plates may be preferred to rods for the stability which they provide. Also, the plates illustrated in the figures are not limiting and as explained for the rods, it may be possible to provide T, V, H, U plates etc. in order to provide better stabilization (by the fact that one in fact has several plates not parallel with each other which oppose the movements in several directions). In certain of these embodiments, said anchor (2) may include a pointed end (21) and/or sharpened edges intended to penetrate the bone tissue (pointed or sharpened designating here means for penetrating the bone). Preferably, said anchor (2) includes an end provided with at least one abutment (22) intended to come into contact with said plate (5) and limit the penetration of the anchor (2) into the bone tissue. The anchor may generally be provided with retaining means in the bone tissue. Thus, as an addition or an alternative to such an abutment, the anchor may include catches avoiding its withdrawal out of the bone or be associated with another locking means such as for example an additional screw, for which at least one portion retains the anchor. Further, according to the provided approach routes and invasivity for the implant, it is possible to provide various shapes for such an anchor. Thus, in certain embodiments, said anchor (2) may be formed with a substantially planar plate (20), while in other embodiments, said anchor (2) may be formed with a substantially curved plate (20). A combination of a flat anchor and of a curved anchor may of course be contemplated. For better stability of the anchor, certain embodiments provide that said anchor (2) and said passage (57) may be laid out for inserting the anchor along an oblique axis relatively to the longitudinal axis, so that the anchor may be oriented from the center to the periphery of the implant during the insertion, as illustrated for example in FIGS. 19A, 19B, 19C, 20A, 20B and 20C. It will be noted that the illustrative examples of these last figures show alternatives which notably differ in that said plate (5) is provided so as to be mounted on (or optionally secured to) the implant and for receiving the anchors which may be locked by a locking means (3) such as a screw or a bolt, as illustrated for example in FIGS. 20A, 20B and 20C. Such a locking means added after insertion of the anchors gives the possibility of locking the assembly. On the other hand, in the examples of FIGS. 19A, 19B and 19C, said plate (5) may be separated from the implant which may be then screwed through the plate (5) receiving the anchors (2). In these examples, the locking may be obtained with the head of the implant which bears upon the anchors as illustrated for example in FIG. 19C or with an additional pin (screw or bolt) of the type of that of FIG. 20B for example.

Figure 21A:
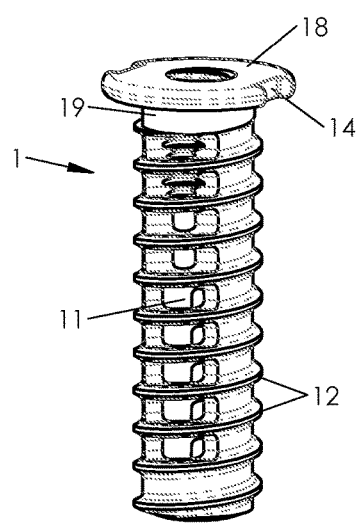
FIGS. 21A and 21C illustrate perspective views of an implant and of stabilization and locking means, before and after assembling, respectively, according to various embodiments
Figure 21B:
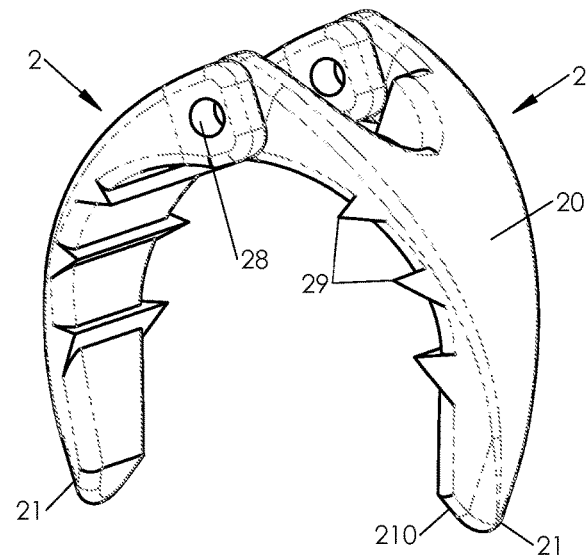
FIG. 21B illustrates a perspective view of such stabilization means.
Figure 21C:
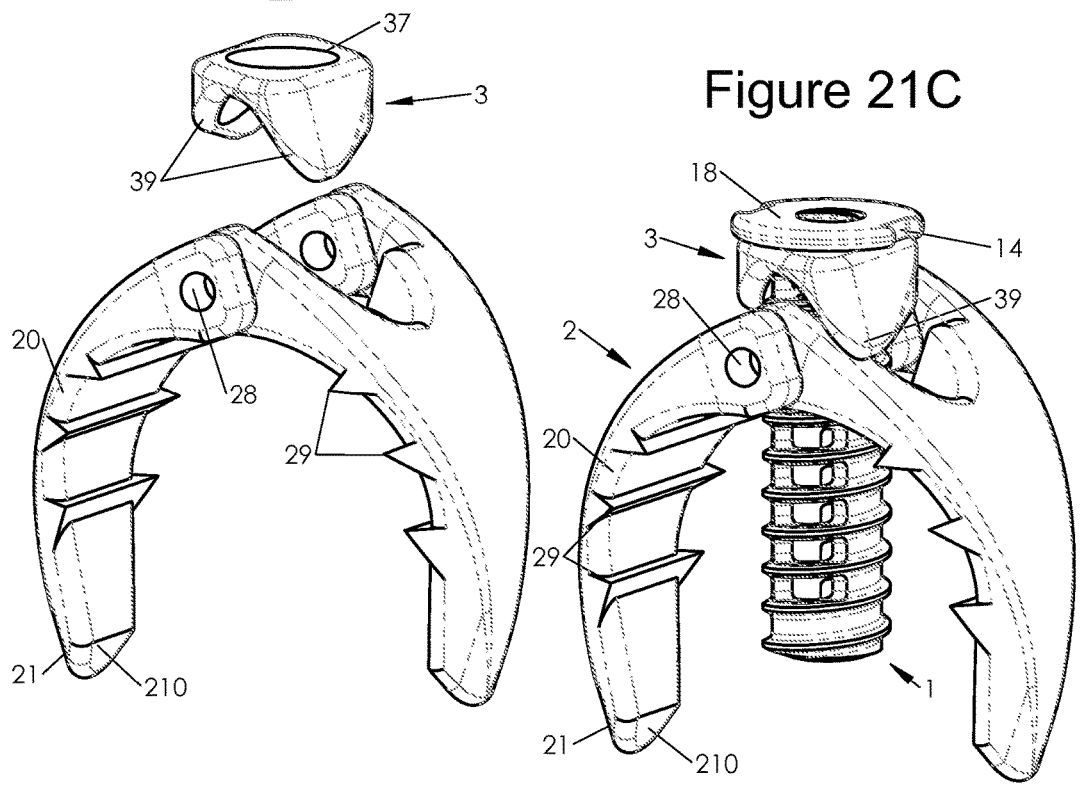

In other embodiments illustrating the possible diversity of the stabilization means, it may be possible to provide at least one stabilization element (2) in the form of a jaw comprising two curved bits (20) each comprising a free end (21) and jointed with each other through two joints (28) separated from each other by a space with a size substantially equal to the size of the head (18), as illustrated for example in FIGS. 21A, 21B and 21C. In this type of layout, the jaw may be mounted around the head and the bits may come into contact with the bone tissues around the body (10) of the implants in order to stabilize the assembly; in these embodiments, said stabilization means preferably may include locking means (3) bearing upon the stabilization element (2) for maintaining it pressed against the bone tissue. In certain of these embodiments, the bits (20) of said jaw (2) may include on their concave face, at least one catch (29) for stabilizing them against the bone tissue. Further, in certain embodiments, the free end (21) of the bits (20) may include at least one chamfer (210) facilitating the opening of the jaw (2) upon inserting the implant into the bone tissue.

The present application describes various technical features and advantages with reference to the figures and/to diverse embodiments. The person skilled in the art will understand that the technical features of a given embodiment may in fact be combined with features of another embodiments unless the opposite is explicitly mentioned or if it is only obvious that these features are incompatible or if the combination does not operate or does not provide solution to at least one of the technical problems of the field, in particular those mentioned in the present application. Further, the technical features described in a given embodiment may be isolated from the other features of this embodiment unless the opposite is explicitly mentioned, notably by the functional considerations provided in the present application and the detailed structural specificities in the description and the figures of the present application.

It should be obvious for skilled practitioners that the present disclosure allows various embodiments under many other specific forms without departing from the field of application. Therefore, the present embodiments should not be considered as limiting illustrations, but rather may be modified within the field and the claimed inventions should not be limited to the details given above.

The invention claimed is:

1. A bone implant comprising a body elongated along a longitudinal axis between a first end of the body and a second end of the body, the body comprising a rounded exterior surface portion disposed proximal to the first end and having a rounded cross-section transverse to the longitudinal axis;
   a head comprising a peripheral lower surface including a spherical portion, the head disposed proximal to the second end of the body;
   a bore extending through at least a portion of the body along the longitudinal axis and opening through the first end of the body;
   a window disposed along the body and forming an opening extending from the bore through the rounded exterior surface portion, with the opening comprising a sharpened edge configured for cutting bone during rotation of the body about the longitudinal axis; and
   a thread winding around at least a portion of the rounded exterior surface portion.

2. A bone implant comprising a body elongated a longitudinal axis between a first end of the body and a second end of the body, the body comprising a rounded exterior surface portion disposed proximal to the first end and having a rounded cross-section transverse to the longitudinal axis;
   a head integrally formed with the body and disposed proximal to the second end of the body, the head including a major diameter larger than the rounded cross-section;
   a bore extending through at least a portion of the body along the longitudinal axis and opening through the first end of the body;
   a window disposed along the body and forming an opening extending from the bore through the rounded exterior surface portion, with the window comprising a cutting edge positioned to engage an adjacent bone during rotation of the body around the longitudinal axis; and
   a thread winding around at least a portion of the rounded exterior surface portion with a portion of the thread extending over the window.

3. The implant of claim 2 in which the body has a substantially frustoconical shape.

4. The implant of claim 3 in which the thread has a perimeter that is substantially cylindrical.

5. The implant of claim 2 comprising plural windows aligned along an axis substantially parallel to the longitudinal axis.

6. A bone implant comprising:
   a body elongated along a longitudinal axis between a first end of the body and a second end of the body, the body comprising a rounded exterior surface portion disposed proximal to the first end and having a rounded cross-section transverse to the longitudinal axis;
   a head integrally formed with the body and disposed proximal to the second end of the body, the head including a major diameter larger than the rounded cross-section;
   a bore extending through at least a portion of the body along the longitudinal axis and opening through the first end of the body;
   a thread winding around at least a portion of the rounded exterior surface portion of the body; and
   a plurality of windows disposed along a portion of the body and forming openings between the thread winding extending from the bore through the rounded exterior surface portion, each window of the plurality of windows incrementally increasing in size from a proximal end to a distal end of the portion of the body.

* * * * *